United States Patent [19]

Oxford et al.

[11] Patent Number: 4,855,314

[45] Date of Patent: Aug. 8, 1989

[54] INDOLE DERIVATIVES

[75] Inventors: Alexander W. Oxford, Royston; Ian H. Coates, Hertfordshire; David E. Bays, Ware; Colin F. Webb, Royston; Michael D. Dowle, Ware; Keith Mills, Ware; Colin D. Eldred, Ware, all of England

[73] Assignee: Glaxo Group Limited, London, England

[21] Appl. No.: 1,469

[22] Filed: Jan. 8, 1987

[30] Foreign Application Priority Data

Jan. 8, 1986 [GB] United Kingdom ............... 8600397

[51] Int. Cl.$^4$ .................. A61K 31/40; C07D 211/26; C07D 211/28
[52] U.S. Cl. .................................. 514/415; 548/504
[58] Field of Search ...................... 548/504; 514/415

[56] References Cited

U.S. PATENT DOCUMENTS 3,472,870 10/1969 Larsen et al. .................. 548/507
4,064,255 12/1977 Champseix et al. ............ 548/504
4,636,521 1/1987 Coates et al. .................. 548/507

FOREIGN PATENT DOCUMENTS 2081717A 2/1982 United Kingdom .
2083463A 3/1982 United Kingdom .

OTHER PUBLICATIONS

Handbook of Experimental Pharmacology, vol. XIX, Springer–Verlag, New York, 1966, pp. 126–129.
Sollmann, A manual of pharmacology 8th Ed., pp. 45–47.
Bradley et al., Proposals for the Classification and Nomenclature of Functional Receptors and 5-hydroxytryptamine, Neuropharmacology, vol. 25, No. 6, pp. 563–576, 1986.
Pharmacological Principles and Practice, Paton, pp. 1–2, 1968.
The Pharmacological Basis of Therapeutics, 7th Ed., pp. 35–37.
Evidence for Two Types of Excitatory Receptor for 5-hydroxytryptamine in Dog Isolated Vasculature, Apperley, pp. 215–223, Re J. Pharmac (1980).

Primary Examiner—Mark L. Berch
Attorney, Agent, or Firm—Bacon & Thomas

[57] ABSTRACT

Compounds are disclosed of formula (I):

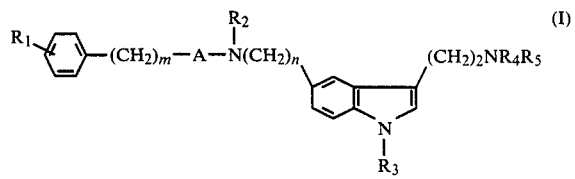

wherein $R_1$ is halogen, a $C_{1-3}$ alkoxy, $R_6R_7NCO(CH_2)_p-$, $R_6CONH(CH_2)_p-$, $R_6R_7NSO_2(CH_2)_p-$, or $R_8SO_2NH(CH_2)_p-$ (where $R_6$ and $R_7$ each represents hydrogen or $C_{1-3}$ alkyl, $R_8$ represents $C_{1-3}$ alkyl and p is zero or 1);

$R_2$ represents hydrogen or $C_{1-3}$ alkyl; $R_3$ represents hydrogen or $C_{1-3}$ alkyl;

$R_4$ and $R_5$ each represents hydrogen, $C_{1-3}$ alkyl or 2-propenyl;

A represents —CO— or —SO$_2$—;

n represents an integer from 2 to 5; and m represents zero or an integer from 1 to 4; and physiologically acceptable salts and solvates (e.g. hydrates) thereof.

The compounds have potent and selective vasoconstrictor activity and are indicated as useful for the treatment of migraine. The compounds may be formulated as pharmaceutical compositions with physiologically acceptable carriers or excipients for administration by any convenient route. Various methods for the preparation of the compounds (I) are disclosed.

10 Claims, No Drawings

INDOLE DERIVATIVES

This invention relates to indole derivatives, to processes for their preparation, to pharmaceutical compositions containing them and to their medical use, in particular to compounds and compositions of use in the treatment of migraine.

The pain of migraine is associated with excessive dilatation of the cranial vasculature, and known treatments for migraine include the administration of compounds having vasoconstrictor properties, such as ergotamine. However, ergotamine is a non-selective vasoconstrictor which constricts blood vessels throughout the body and has undesirable and dangerous side effects. Migraine may also be treated by administering an analgesic, usually in combination with an antiemetic, but such treatments are of limited value.

There is thus a need for a safe and effective drug for the treatment of migraine, which can be used either prophylactically or to alleviate an established headache, and a compound having a selective vasoconstrictor activity would fulfil such a role.

We have now found a group of indole derivatives having potent and selective vasoconstrictor activity.

The present invention provides an indole of the general formula (I):

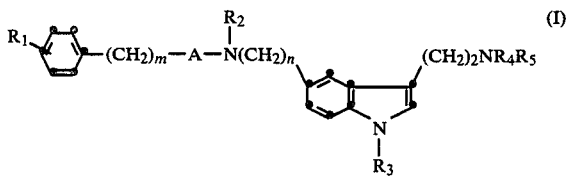

wherein
$R_1$ represents a halogen atom, a $C_{1-3}$ alkoxy group, a group $R_6R_7NCO(CH_2)_p$—, a group $R_6CONH(CH_2)_p$—, a group $R_6R_7NSO_2(CH_2)_p$—, or a group $R_8SO_2NH(CH_2)_p$— (where $R_6$ and $R_7$, which may be the same or different, each represents a hydrogen atom or a $C_{1-3}$ alkyl group, $R_8$ represents a $C_{1-3}$ alkyl group and p is zero or 1);
$R_2$ represents a hydrogen atom or a $C_{1-3}$ alkyl group; $R_3$ represents a hydrogen atom or a $C_{1-3}$ alkyl group;
$R_4$ and $R_5$ which may be the same or different, each represents a hydrogen atom, a $C_{1-3}$ alkyl group or a 2-propenyl group;
A represents —CO— or —SO$_2$—;
n represents an integer from 2 to 5; and m represents zero or an integer from 1 to 4; and physiologically acceptable salts and solvates (e.g. hydrates) thereof.

The invention includes within its scope all optical isomers of compounds of formula (I) and their mixtures, including the racemic mixtures thereof.

In the compounds of general formula (I) it will be appreciated that the substituent $R_1$ may be in the ortho, meta or para positions.

Referring to the general formula (I), the alkyl groups may be straight chain or branched chain alkyl groups, such as methyl, ethyl or isopropyl groups. A $C_{1-3}$ alkoxy group may be for example methoxy, and a halogen substituent may be for example fluorine, chlorine or bromine.

The substituent $R_1$ in compounds of formula (I) may be for example a chlorine atom or a group such as methoxy, $H_2NCO$—, $H_2NCOCH_2$—, $CH_3NHCO$—, $CH_3NHCOCH_2$—, $(CH_3)_2NCO$—, $(CH_3)_2NCOCH_2$—, $CH_3CONH$—, $CH_3CONHCH_2$—; $H_2NSO_2$—, $H_2NSO_2CH_2$—, $CH_3NHSO_2$—, $CH_3NHSO_2CH_2$—, $(CH_3)_2NSO_2CH_2$—, $CH_3SO_2NH$—, or $CH_3SO_2NHCH_2$—.

In one general preference, $R_1$ is a chlorine atom or a methoxy group.

In another general preference $R_1$ is a $H_2NCOCH_2$—, $CH_3NHCOCH_2$—$(CH_3)_3)_2NCOCH_2$—, $CH_3CONH$—, $CH_3CONHCH_2$—, $H_2NSO_2$—, $CH_3SO_2NH$— or $CH_3SO_2NHCH_2$— group.

m may be zero or an integer 2, 3 or 4, but in general is preferably an integer 1.

n may be an integer 3, 4 or 5, but in general is preferably an integer 2.

The group A may be —SO$_2$—, but is preferably —CO—.

A preferred class of compounds represented by the general formula (I) is that wherein $R_2$ represents a hydrogen atom. A further preferred class of compounds is that in which $R_3$ represents a hydrogen atom.

A still further preferred class of compounds is that in which $R_4$ and $R_5$ which may be the same or different each represents a hydrogen atom or a methyl or ethyl group. It is preferred that the total number of carbon atoms in $R_4$ and $R_5$ does not exceed two.

A particularly useful group of compounds according to the invention has the formula (Ia)

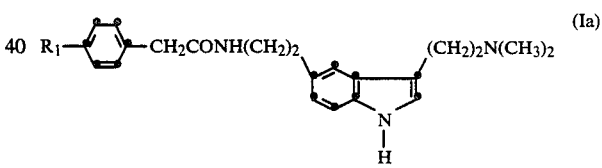

in which
$R_1$ is a chlorine atom or a methoxy group or is a, $H_2NCOCH_2$—, $CH_3NHCOCH_2$—, $(CH_3)_2NCOCH_2$—, $CH_3CONH$—, $CH_3CONHCH_2$—, $H_2NSO_2$—, $CH_3SO_2NH$— or $CH_2SO_2NHCH_2$— group;
and physiologically acceptable salts and solvates (e.g. hydrates) thereof.

Particularly important compounds of this type are those in which $R_1$ is a $H_2NCOCH_2$—, $CH_3NHCOCH_2$—, $CH_3SO_2NHCH_2$—, or $H_2NSO_2$— group, or, especially, a $CH_3CONH$— or $CH_3SO_2NH$— group.

A preferred compound according to the invention is: 4-(acetylamino)-N-[2-[3-[2-(dimethylamino)ethyl]-1H-indol-5-yl]ethyl]benzeneacetamide and its physiologically acceptable salts and solvates (e.g. hydrates).

Suitable physiologically acceptable salts of the indoles of general formula (I) include acid addition salts formed with inorganic or organic acids, for example hydrochlorides, hydrobromides, sulphates, nitrates, phosphats, oxalates, tartrates, citrates, fumarates, maleates, succinates, and sulphonates e.g. mesylates. Other salts may be useful in the preparation of compounds of formula (I) e.g. creatinine sulphate adducts.

It will be appreciated that the invention extends to other physiologically acceptable equivalents of the compounds according to the invention, i.e. physiologically acceptable compounds which are converted in vivo into the parent compound. Examples of such equivalents include physiologically acceptable, metabolically labile, N-acyl derivatives.

Compounds of the invention potently and selectively constrict the carotid arterial bed of the anaesthetised dog, whilst having a negligible effect on blood pressure. This potent and selective vasoconstrictor action has been demonstrated in vitro.

Compounds of the invention are useful in treating pain resulting from dilatation of the carotid vascular bed, in particular migraine and cluster headache.

Accordingly, the invention also provides a pharmaceutical composition adapted for use in human medicine which comprises at least one compound of formula (I) or a physiologically acceptable salt or solvate (e.g. hydrate) thereof and formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbital syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

The compounds of the invention may be formulated for parenteral administration by injection. Formulations for injection may be presented in unit dosage form e.g. in ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

For administration by inhalation the compounds according to the invention are conveniently delivered in the form of an aerosol spray presentation from pressurised packs, with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for oral, parenteral, buccal or rectal administration to man (of average bodyweight e.g. about 70 kg) for the treatment of migraine is 0.03 to 100 mg preferably 0.03 to 30 mg of the active ingredient per unit dose which could be administered, for example, 1 to 4 times per day. It will be appreciated that it may be necessary to make routine variations to the dosage depending on the age and weight of the patient as well as the severity of the condition to be treated.

For oral administration a unit dose will preferably contain from 0.3 to 30 mg of the active ingredient. A unit dose for parenteral administration will preferably contain 0.1 to 5 mg of the active ingredient.

Aerosol formulations are preferably arranged so that each metered dose or 'puff' delivered from a pressurised aerosol contains 0.1 to 2 mg of a compound of the invention and each dose administered via capsules or cartridges in an inhaler or insufflator contains 0.2 to 10 mg. The overall daily dose by inhalation will be within the range 0.3 mg to 30 mg. Administration may be several times daily, for example from 2 to 8 times, giving for example 1, 2 or 3 doses each time.

The compounds of the invention may, if desired, be administered in combination with one or more other therapeutic agents, such as analgesics, anti-inflammatory agents and anti-nauseants.

According to another aspect of the invention, compounds of formula (I), and physiologically acceptable salts or solvates (e.g. hydrates) thereof, may be prepared by the general methods outlined below. In the following processes, $R_1$, $R_2$, $R_3$, $R_4$, $R_5$, A, m and n are as defined for the general formula (I) unless otherwise specified.

According to one general process (A), a compound of general formula (I) may be prepared by reacting a compound of general formula (II):

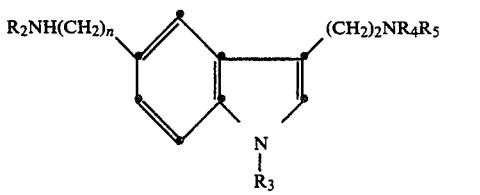

or a salt thereof (for example, an organic or inorganic acid addition salt such as the hydrochloride, hydrobromide, maleate, sulphate or creatinine sulphate adduct) or an N-silyl derivative thereof or a protected derivative thereof with a reagent serving to introduce the group

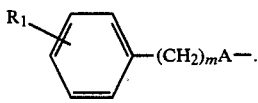

Suitable reagents which serve to introduce the group

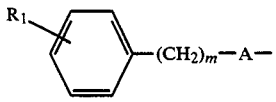

include acids of the general formula

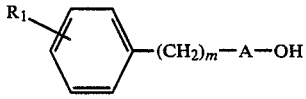

or acylating agents corresponding thereto.

Acylating agents which may conveniently be used in the above process include acid halides (for example carboxylic acid chlorides and sulphonyl chlorides), alkyl esters, (for example the methyl or ethyl ester), activated esters (for example the 2-(1-methylpyridinyl)ester), symmetrical anhydrides, mixed anhydrides or other activated carboxylic acid derivatives such as those conveniently used in peptide synthesis.

The process may be effected in a suitable aqueous or non-aqueous reaction medium, conveniently at a temperature of from −70° to +150° C. Thus the process using an acid halide, an activated ester or an anhydride may be effected in a suitable reaction medium such as an amide (e.g. N,N-dimethylformamide) or hexamethylphosphoramide, an ether (e.g. tetrahydrofuran), a nitrile (e.g. acetonitrile), a haloalkane (e.g. dichloromethane) or mixtures thereof, optionally in the presence of an organic base, for example a tertiary amine such as triethylamine or pyridine, or an inorganic base such as potassium carbonate or sodium bicarbonate. The organic base may also serve as a reaction solvent. The reaction is preferably effected at a temperature of from −15° to +25° C., for example −5° to +25° C.

The reaction using an alkyl ester may be effected in a suitable reaction medium such as an alcohol (e.g. methanol), an amide (e.g. dimethylformamide), an ether (e.g. tetrahydrofuran) or mixtures thereof and conveniently at a temperature of from 0° to 100° C.

Where A represents —CO— carboxylic acids of formula

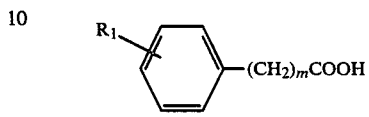

may also be used in the preparation of compounds of formula (I). The reaction is desirably conducted in the presence of a coupling agent for example N,N'-carbonyldiimidazole or a carbodiimide such as N,N'-dicyclohexylcarbodiimide. The reaction may be carried out in a suitable reaction medium such as a haloalkane (e.g. dichloromethane), a nitrile (e.g. acetonitrile), an amide (e.g. dimethylformamide) or an ether (e.g. tetrahydrofuran) or mixtures thereof conveniently at a temperature of from −50° to +50° C., preferably −5° to +30° C. The reaction may also be carried out in the absence of a coupling agent in a suitable reaction medium such as a hydrocarbon (e.g. toluene or xylene) conveniently at a temperature of from 50° to 120° C.

Compounds of general formula (II) are novel and comprise a further feature of the invention.

Compounds of general formula (II) wherein $R_2$ is a hydrogen atom may be prepared for example by reduction of a corresponding compound having an appropriate reducible group as the 5-position substituent, such as —$(CH_2)_{n-1}CN$. The reduction may be effected by catalytic hydrogenation, or using a reducing agent such as lithium aluminum hydride.

Such nitrile compounds are novel and constitute a further feature of the invention. They may be prepared for example by cyclisation of the appropriate hydrazone, in an analogous manner to general process (B), described hereinafter.

Compounds of general formula (II) wherein $R_2$ is an alkyl group may be prepared for example by reduction of a corresponding nitrile in the presence of an amine $R_2NH_2$, or by reacting a compound of formula (II) wherein $R_2$ is a hydrogen atom with a suitable alkylating agent.

According to another general process (B), compounds of formula (I) may be prepared by the cyclisation of a compound of general formula (III):

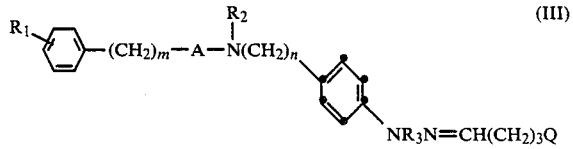

wherein Q is the group $NR_4R_5$ (or a protected derivative thereof) or a leaving atom or group such as a halogen atom (e.g. chlorine or bromine) or an acyloxy group, (e.g. a carboxylic or sulphonic acyloxy group such as an acetoxy, chloracetoxy, dichloroacetoxy, trifluoroacetoxy, p-nitrobenzoyloxy, p-toluenesulphonyloxy or methanesulphonyloxy group).

The reaction may conveniently be effected in aqueous or non-aqueous reaction media, and at temperatures of from 20° to 200° C., preferably 50 to 125° C.

Particularly convenient embodiments of the process are described below.

When Q is the group NR₄R₅ (or a protected derivative thereof) the process is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

Alternatively the cyclisation may be carried out in an aqueous or non-aqueous reaction medium, in the presence of an acid catalyst. When an aqueous medium is employed this may be an aqueous organic solvent such as an aqueous alcohol (e.g. methanol, ethanol or isopropanol) or an aqueous ether (e.g. dioxan or tetrahydrofuran) as well as mixtures of such solvents. The acid catalyst may be for example an inorganic acid such as concentrated hydrochloric or sulphuric acid or an organic acid such as acetic acid. (In some cases the acid catalyst may also act as the reaction solvent). In an anhydrous reaction medium, which may comprise for example one or more ethers (e.g. as previously described) or esters (e.g. methyl acetate), the acid catalyst will generally be a Lewis acid such as boron trifluoride, zinc chloride or magnesium chloride.

When Q is a leaving atom or group such as a chlorine or bromine atom the reaction may be effected in an aqueous organic solvent, such as an aqueous alcohol (e.g. methanol, ethanol or isopropanol) in the absence of an acid catalyst, conveniently at a temperature of from 20° to 200° C., preferably 50° to 125° C. This process results in the formation of a compound of formula (I) wherein R₄ and R₅ are both hydrogen atoms.

According to a particular embodiment of this process compounds of formula (I) may be prepared directly by the reaction of a compound of general formula (IV):

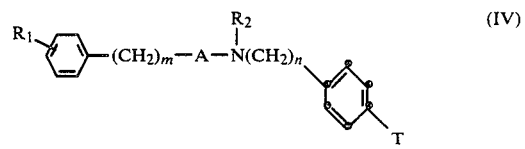

(where T is a group NR₃NH₂) or a salt thereof, with a compound of formula (V):

(wherein Q is as defined above) or a salt or protected derivative thereof (such as an acetal or ketal e.g. formed with an appropriate alkyl orthoformate or diol, or protected as a bisulphite addition complex) using the appropriate conditions are described above for the cyclisation of compounds of general formula (III). It will be appreciated that in this embodiment of the cyclisation process (B) a compound of general formula (III) is formed as an intermediate, and may be reacted in situ to form the desired compound of general formula (I).

Compounds of general formula (III) may, if desired, be isolated as intermediates during the process for the preparation of compounds of formula (I) wherein a compound of formula (IV), or a salt or protected derivative thereof, is reacted with a compound of formula (V), or a salt or protected derivative thereof, in water or in a suitable aqueous alcohol (e.g. methanol) at a temperature of, for example, 20° to 30° C. If an acetal or ketal of a compound of formula (V) is used, it may be necessary to carry out the reaction in the presence of an acid (for example, acetic or hydrochloric acid).

Compounds of general formula (IV) may be prepared for example from the corresponding nitro compounds (i.e. in which T is NO₂), using conventional procedures.

A further general process (C) for preparing compounds of general formula (I) involves reacting a compound of general formula (VI):

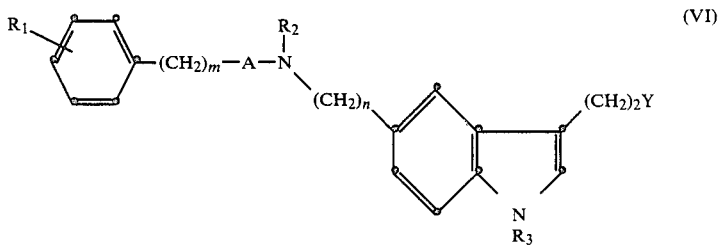

(wherein Y is a readily displaceable atom or group) or a protected derivative thereof, with an amine of formula R₄R₅NH.

The displacement reaction may conveniently be carried out on those compounds of formula (VI) wherein Y is a halogen atom (e.g. chlorine, bromine or iodine) or a group OR₉ where OR₉ is, for example, an acyloxy group which may be derived from a carboxylic or sulphonic acid, such as an acetoxy, chloroacetoxy, dichloroacetoxy, trifluoroacetoxy, p-nitrobenzoyloxy, p-toluenesuphonyloxy or methanesulphonyloxy group.

The displacement reaction may be conveniently effected in an inert organic solvent (optionally in the presence of water), examples of which include alcohols, e.g. ethanol; cyclic ethers, e.g. dioxan or tetrahydrofuran; acylic ethers e.g. diethylether, esters, e.g. ethyl acetate; amides, e.g. N,N-dimethylformamide; and ketones e.g. acetone or methylethyl ketone, at a temperature of from $-10°$ to $+150°$ C., preferably 20° to 50° C.

The compounds of general formula (VI) wherein Y is a halogen atom may be prepared by reacting a hydrazine of general formula (IV) with an aldehyde or ketone (or a protected derivative thereof) of formula (V) in which Q is a halogen atom, in an aqueous alcohol (e.g. methanol) containing an acid (e.g. acetic or hydrochloric acid). Compounds of formula (VI) wherein Y is the group $OR_9$ may be prepared from the corresponding compound wherein Y is a hydroxyl group by acylation with the appropriate activated species (e.g. anhydride or sulphonyl chloride) using conventional techniques. The intermediate alcohol may be prepared by cyclisation of a compound of formula (III) wherein Q is a hydroxyl group (or a protected derivative thereof) under standard conditions.

Compounds of formula (I) may also be prepared by another general process (D) involving reduction of a compound of general formula (VII):

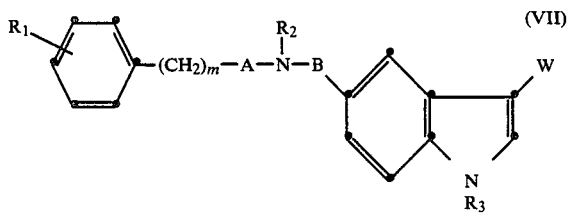

(wherein W is a group capable of being reduced to give the required $-(CH_2)_2NR_4R_5$ group or to give a protected derivative of $-(CH_2)_2NR_4R_5$; and B represents the group $-(CH_2)_n-$ as herein defined or a group capable of being reduced to $-(CH_2)_n-$) or a salt or protected derivative thereof.

The required $-(CH_2)_2-$ and $-NR_4R_5$ groups at the 3-position may be formed by reduction steps which take place separately or together in any appropriate manner.

Groups B which may be reduced to give the required group $-(CH_2)_n-$ include corresponding unsaturated groups, such as $C_{2-5}$ alkenyl or alkynyl groups.

Examples of groups represented by the substituent W include $-(CH_2)_2NO_2$; $-CH=CHNO_2$; $-(CH_2)_2N_3$; $-CH_2CN$; $-CH_2CHO$; $-COCH_2Z$; $-CH_2CH=NOH$; $-CH(OH)CH_2NR_4R_5$; $-(CH_2)_2NR_4COR'_5$; $-COCONR_4R_5$ and $-CH_2COZ$ (wherein Z is an azido group or the group $-NR_4R_5$ or a protected derivative thereof and $R'_5$ is a hydrogen atom or a methyl or ethyl group or $R'_5$ represents the group $OR_{10}$ where $R_{10}$ is an alkyl or aralkyl group).

Groups which may be reduced to the $-(CH_2)_2-$ moiety at the 3-position include the corresponding unsaturated group and corresponding groups containing one or more hydroxyl groups or carbonyl functions.

Groups which may be reduced to the group $-NR_4R_5$ where $R_4$ and $R_5$ are both hydrogen include nitro, azido, hydroxyimino and nitrile groups. In the latter case, reduction yields the group $-CH_2NH_2$ and thus provides a methylene group of the $-(CH_2)_2-$ moiety.

A compound of general formula (I) where $R_5$ is a hydrogen atom may also be prepared by reduction of a corresponding compound wherein $R_5$ is a benzyl group, e.g. with hydrogen in the presence of a catalyst, e.g. 10% palladium on charcoal.

The required $-NR_4R_5$ group wherein $R_4$ and/or $R_5$ are other than hydrogen may be prepared by reduction of a nitrile $-CH_2CN$ or an aldehyde $-CH_2CHO$ in the presence of an amine, $R_4R_5NH$.

A particularly suitable method for preparing a compound of formula (I) wherein $R_4$ and/or $R_5$ is other than hydrogen is reductive alkylation of the corresponding compound wherein $R_4$ and/or $R_5$ represent hydrogen with an appropriate aldehyde or ketone (e.g. acetaldehyde or acetone) in the presence of a suitable reducing agent. Suitable reducing agents for use in this process include hydrogen in the presence of a metal catalyst, or an alkali metal borohydride or cyanoborohydride (for example, sodium borohydride or cyanoborohydride) using the conditions described below for the reduction of compounds of formula (VII). In some instances (e.g. for the introduction of the group $R_5$ where $R_5$ is ethyl) the aldehyde (e.g. acetaldehyde) may be condensed with the amine and the intermediate thus formed may subsequently be reduced using a suitable reducing agent.

The required $-NR_4R_5$ group wherein $R_4$ and/or $R_5$ are other than hydrogen may also be prepared by reduction of a corresponding acylamino group, e.g. of the formula $-(CH_2)_2NR_4COR'_5$ where $R'_5$ is as previously defined).

It will be appreciated that the choice of reducing agent and reaction conditions will be dependent on the nature of the groups W, B and other groups already present on the molecule. It will also be appreciated that when A represents $-CO-$ the group W will not contain an amide function.

Suitable reducing agents which may be used in the above process for the reduction of compounds of formula (VII) wherein W represents, for example, the groups $-(CH_2)_2NO_2$; $-CH=CHNO_2$, $-(CH_2)_2N_3$, $-CH_2CN$, $-CH_2CH=NOH$ and $-CH(OH)CH_2NR_4R_5$ include hydrogen in the presence of a metal catalyst, for example Raney Nickel or a noble metal catalyst such as platinum, platinum oxide, palladium, palladium oxide or rhodium, which may be supported, for example on charcoal, kieselguhr or alumina. In the case of Raney Nickel hydrazine may also be used as the source of hydrogen. This process may conveniently be carried out in a solvent such as an alcohol e.g. ethanol, an ether, e.g. dioxan or tetrahydrofuran, an amide, e.g. dimethylformamide or an ester e.g. ethyl acetate, and at a temperature of from $-10°$ to $+50°$ C., preferably $-5°$ to $+30°$ C.

The reduction process may also be effected on compounds of formula (VII) wherein W represents, for example, the groups $-(CH_2)_2NO_2$, $-CH=CHNO_2$, —(CH$_2$)$_2$N$_3$, —CH(OH)CH$_2$NR$_4$R$_5$ or —COCH$_2$Z (where Z is as previously defined), using an alkali metal or alkaline earth metal borohydride or cyanoborohydride e.g. sodium or calcium borohydride or cyanoborohydride which process may conveniently be carried out in an alcohol such as propanol or ethanol or a nitrile such as acetonitrile, and at a temperature of from 10° to 100° C., preferably 50° to 100° C. In some instances the reduction using a borohydride may be carried out in the presence of cobaltous chloride.

When A represents a group —SO$_2$—, reduction of compounds of formula (VII) wherein W represents, for example, —(CH$_2$)$_2$NO$_2$;, —CH═CHNO$_2$, —(CH$_2$)$_2$N$_3$, —(CH$_2$)$_2$NR$_4$COR'$_5$; —CH$_2$CH═NOH, —CH(OH)CH$_2$NR$_4$R$_5$; —COCONR$_4$R$_5$, —CH$_2$COZ and —COCH$_2$Z (wherein R'$_5$ and Z are as previously defined) may also be carried out using a metal hydride such as lithium aluminium hydride. This process may be carried out in a solvent, for example, an ether such as tetrahydrofuran, and conveniently at a temperature of from −10° to +100° C., preferably 50° to 100° C.

A particular embodiment of general process (D) includes the reduction of a compound of formula (VII) wherein W is the group —CH$_2$CN for example, by catalytic reduction with hydrogen in the presence of a catalyst such as palladium on charcoal or rhodium on alumina, optionally in the presence of an amine HNR$_4$R$_5$.

Suitable reducing agents which may be used in the reduction of the group B include hydrogen in the presence of a metal catalyst. Appropriate metal catalysts and conditions for the reduction process are as described for the reduction of the group W.

The starting materials or intermediate compounds of formula (VII) may be prepared by analogous methods to those described in UK published patent application No. 2035310, and 'A Chemistry of Heterocyclic Compounds—Indoles Part II', Chapter VI, edited by W J Houlihan (1972) Wiley Interscience, New York.

Compounds of formula (VII), wherein W is the group —CH$_2$CHO may be prepared by oxidation (e.g. with Jones' reagent) of a compound of formula (VI) wherein Y is a hydroxyl group. A compound of formula (VII) wherein W is the group —CH$_2$CH═NOH may be prepared by treatment of the corresponding aldehyde with hydroxylamine hydrochloride using standard conditions.

The intermediate compound of formula (VII) wherein W is the group —(CH$_2$)$_2$N$_3$ may be prepared from a compound of formula (VI) wherein Y is a halogen atom using standard procedures.

Standard reducing agents such as sodium borohydride may be used to prepare a compound of formula (VII) wherein W is the group —CH(OH)CH$_2$NR$_4$R$_5$ from the corresponding compound of formula (VII) wherein W is the group —COCH$_2$NR$_4$R$_5$.

A compound of formula (VII) wherein W is the group —(CH$_2$)$_2$NR$_4$COR'$_5$ may be prepared by acylation of the corresponding unsubstituted amine using conventional procedures.

The intermediate compounds of formula (VII) wherein B represents a C$_{2-5}$ alkenyl group may be prepared by reacting a compound of general formula (VIII)

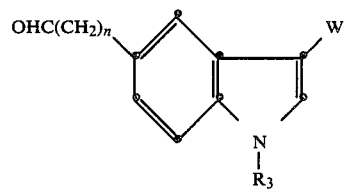

(wherein W is as defined for general formula (VII) and n is zero or an integer of from 1 to 3) with for example an appropriate phosphonium salt, using standard conditions.

According to a further general process (E) a compound of formula (I) according to the invention, or a salt or protected derivative thereof, may be converted into another compound of formula (I) using conventional procedures.

For example, a compound of general formula (I) wherein one or more of R$_3$, R$_4$ and/or R$_5$ are alkyl groups may be prepared from the corresponding compounds of formula (I) wherein one or more of R$_3$, R$_4$ and R$_5$ represent hydrogen atoms, by reaction with a suitable alkylating agent such as a compound of formula R$_x$L, (where R$_x$ represents the desired R$_3$, R$_4$ or R$_5$ group and L represents a leaving atom or group such as a halogen atom or a tosylate group) or a sulphate (R$_x$)$_2$SO$_4$. Thus, the alkylating agent may be for example an alkyl halide (e.g. methyl or ethyl iodide), alkyl tosylate (e.g. methyl tosylate) or dialkylsulphate (e.g. dimethylsulphate).

The alkylation reaction may conveniently be carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides such as sodium or potassium hydride, alkali metal amides such as sodium amide, alkali metal carbonates such as sodium carbonate or alkali metal alkoxide such as sodium or potassium methoxide, ethoxide or t-butoxide; or tetrabutylammonium fluoride. When an alkyl halide is employed as the alkylating agent the reaction may also be carried out in the presence of an acid scavenging agent such as propylene or ethylene oxide. The reaction may be conveniently effected at a temperature of from −20° to 100° C.

Compounds of formula (I) wherein one or both of R$_3$ and R$_4$ represents propenyl may be prepared similarly, using an appropriate compound of formula R$_x$L or (R$_x$)$_2$SO$_4$.

According to another general process (F), a compound of general formula (I) according to the invention, or a salt thereof may be prepared by subjecting a protected derivative of general formula (I) or a salt thereof to reaction to remove the protecting group or groups.

Thus, at an earlier stage in the reaction sequence for the preparation of a compound of general formula (I) or a salt thereof it may have been necessary or desirable to protect one or more sensitive groups in the molecule to avoid undesirable side reactions. For example it may be necessary to protect the group $NR_4R_5$, wherein $R_4$ and/or $R_5$ represents hydrogen, by protonation or with a group easily removable at the end of the reaction sequence. Such groups may include, for example, aralkyl groups, such as benzyl, diphenylmethyl or triphenylmethyl; or acyl groups such as N-benzyloxycarbonyl or t-butoxycarbonyl or phthaloyl.

In some cases, it may also be desirable to protect the indole nitrogen with, for example, an aralkyl group such as benzyl.

Subsequent cleavage of the protecting group or groups may be achieved by, conventional procedures. Thus an aralkyl group such as benzyl, may be cleaved by hydrogenolysis in the presence of a catalyst (e.g. palladium on charcoal) or sodium and liquid ammonia; an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

As will be appreciated, in some of the general processes (A) to (E) described previously it may be necessary or desirable to protect any sensitive groups in the molecule as just described. Thus, a reaction step involving deprotection of a protected derivative of general formula (I) or a salt thereof may be carried out subsequent to any of the previously described processes (A) to (E).

Thus, according to a further aspect of the invention, the following reactions may if necessary and/or desired be carried out in any appropriate sequence subsequent to any of the processes (A) to (E):
(i) removal of any protecting groups; and
(ii) conversion of a compound of general formula (I) or a salt thereof into a physiologically acceptable salt or solvate (e.g. hydrate) thereof.

Where it is desired to isolate a compound of the invention as a salt, for example as an acid addition salt, this may be achieved by treating the free base of general formula (I), with an appropriate acid, preferably with an equivalent amount or with creatinine sulphate in a suitable solvent (e.g. aqueous ethanol).

The starting materials or intermediate compounds for the preparation of the compounds according to this invention may be prepared by analogous methods to those described in UK published patent application No. 2035310.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced before or after cyclisation to form the indole nucleus. It should therefore be appreciated that in such multi-stage processes, the sequence of reactions should be chosen in order that the reaction conditions do not affect groups present in the molecule which are desired in the final product.

The invention is further illustrated by the following Examples. All temperatures are in °C.

Chromatography was carried out either in the conventional manner using silica gel (Merck, Kieselgel 60, Art. 7734) or by flash chromatography (W. C. Still, M. Kahn and A. Mitra, J. Org. Chem. 2933, 43, 1978) on silica gel (Merck Keisolgel 60, Art. 9385) and thin layer chromatography (t.l.c.) on silica (Macherly-Nagel, Polygram) except where otherwise stated. The following abbreviations define the eluants used for chromatography and t.l.c.: (A)→(H)=$CH_2CL_2$-ethanol-0.88 ammonia in the following ratios (A)-89:10:1, (B)-78:20:2, (C)-50:8:1, (D)-83.5:15:1.5, (E)-75:8:1, (F)-25:8:1, (G)-50:10:1, (H)-100:8:1; (I) ethyl acetate-methanol-triethylamine-80:20:1.

The following abbreviations are used: THF-tetrahydrofuran; ER-ether; EA-ethyl acetate.

Intermediates were routinely checked for purity by t.l.c. employing u.v. light for detection and spray reagents such as potassium permanganate ($KMnO_4$). In addition indolic intermediates were detected by spraying with aqueous ceric sulphate (CeIV) and tryptamines by spraying with a solutoin of iodoplatinic acid (IPA) or ceric sulphate.

Proton ($^1H$) nuclear magnetic resonance (n.m.r.) spectra were obtained either at 90 MHz using a Varian EM 390 instrument or at 250 MHz using a Bruker AM or WM 250 instrument. s=singlet, d=doublet, t=triplet, m=multiplet and q=quartet.

Intermediate 1

4-Hydrazinobenzeneacetonitrile hydrochloride

A solution of sodium nitrite (4.0 g) in water (34 ml) was added dropwise at −5° to −2° to a suspension of 4-aminobenzeneacetonitrile (7.6 g) in concentrated hydrochloric acid (80 ml), and stirring was continued at −2° for 20 min. The mixture was filtered and the filtrate added dropwise at 0° to 5° to a solution of tin (II) chloride dihydrate (65 g) in concentrated hydrochloric acid (130 ml). The mixture was allowed to warm to room temperature overnight (17 h), and the precipitate was filtered off, washed with concentrated hydrochloric acid, cold absolute ethanol, and dry ER, and dried to give the title salt as a powder (6.05 g). m.p. 207°–210° (foams).

Intermediate 2

4-[2-[4-(Dimethylamino)butylidene]hydrazino]benzeneacetonitrile 4,4-Diethoxy-N,N-dimethylbutanamine (9.45 g) was added to a stirred suspension of Intermediate 1 (9.2 g) in deionized $H_2O$ (200 ml) at room temperature under nitrogen, 2N hydrochloric acid (22 ml) was added (pH2), and stirring was continued at room temperature for 5 h. The clear solution was basified with 8% aqueous $NaHCO_3$ (200 ml) and extracted with $CHCL_3$ (3×200 ml). The organic layers were dried ($MgSO_4$) and evaporated to give the title compound as an oil (15.6 g). T.l.c. (Silica, A) Rf 0.35 detection uv/IPA.

Intermediate 3

5-(Cyanomethyl)-N,N-dimethyl-1H-indole-3-ethanamine oxalate

Intermediate 2 (15.4 g) was heated under reflux with polyphosphate ester (108 g) in CHCl$_3$ (200 ml) with stirring under nitrogen for 8 min. The mixture was poured onto ice, 8% aqueous NaHCO$_3$ (500 ml) was added, and after 20 min stirring the layers were separated and the aqueous layer extracted with CHCl$_3$ (3×400 ml). The aqueous layer was further basified to pH 9 with 2N Na$_2$CO$_3$ (200 ml), solid NaCl was added, and the mixture was extracted with CHCl$_3$ (3×400 ml). The combined organic layers were dried (MgSO$_4$) and evaporated to give an oil (40.2 g). The oil was partitioned between EA (200 ml) and 2N hydrochloric acid (4×40 ml); the aqueous layers were basified (200 ml 2N and 20 ml 5N NaOH) and extracted with EA (4×100 ml). The latter organic layers were washed with brine, dried (MgSO$_4$) and evaporated to give an oil (9.3 g). Purification by flash chromatography (A and D) gave a first crop (1.91 g) as an oil and a second crop (4.0 g) also as oil. The second crop oil was dissolved in hot methanol (10 ml), and oxalic acid (1.59 g) in hot methanol was added. On cooling, crystals were deposited and after cooling in ice, the crystals were filtered off, washed with methanol and dried to give the title compound (4.0 g) m.p. 183.5°–187°. The pure first crop was converted similarly to the oxalate salt (2.15 g).

Intermediate 4

N$^3$,N$^3$-Dimethyl-1H-indole-3,5-diethanamine dioxalate

Intermediate 3 (3.17 g) was partitioned between 8% aqueous NaHCO$_3$ (100 ml) and CH$_2$Cl$_2$ (3×80 ml) and the organic layers dried (MgSO$_4$) and evaporated to give the free base as an oil (2.41 g). The oil was hydrogenated at 45° and 70 psi over 5% rhodium on alumina (1.0 g) in 7% w/w ethanolic ammonia (200 ml) for 15.5 h. The catalyst was filtered off and the solvent evaporated to give the title compound, free base as an oil (2.58 g). A portion (1.37 g) of the oil was dissolved in methanol (6 ml), and oxalic acid (1.12 g) was added in methanol (2 ml). Addition of dry ER (80 ml) gave a gum, which was triturated with dry ER to afford the title compound as a solid (1.79 g) m.p. 160°–170° (foams).

Intemediate 5

4-(Aminocarbonyl)benzeneacetic acid

A mixture of ethyl 4-cyanobenzeneacetate (1.9 g) and freshly ground KOH (2.8 g) in 2-methylpropan-2-ol (20 ml) was heated under gentle reflux for 20 min. The resulting mixture was cooled, diluted with 50% saturated NaCl solution (50 ml), washed with CHCl$_3$ (4×50 ml), and acidified with 2M hydrochloric acid (25 ml) to precipitate the title compound (1.65 g) as a fine white solid m.p. 226°–227°.

Intermediate 6

Phenyl 4-[(methylsulphonyl)amino]benzenemethanesulphonate

Methanesulphonyl chloride (1.12 ml) was added to a cooled stirred solution of phenyl 4-aminobenzenemethanesulphonate, hydrochloride (3.0 g) in pyridine (9 ml). The resulting mixture was allowed to warm up to 20° and then stirred for 20 h. The reaction mixture was diluted with EA (150 ml) and washed with 8% NaHCO$_3$ (400 ml), H$_2$O (250 ml) and brine (250 ml). The organic extract was dried (MgSO$_4$) and evaporated to leave a brown gum which was crystallised from toluene (100 ml) to give the crude title compound (as an off-white solid which was recrystallised from toluene (100 ml) to give the title compound (1.25 g) as a white solid m.p. 128°–129°.

Intermediate 7

4-[2-(Methylamino)-2-oxoethyl]benzeneacetic acid

A mixture of N,N'-carbonyldiimidazole (4.86 g) and 1,4-phenylenediacetic acid (5.8 g) in dry distilled THF (250 ml) was stirred under nitrogen at reflux for 2 h. The reaction mixture was cooled to 20° and methylamine gas (about 6 g) was bubbled through. The mixture was then refluxed for 3 h, cooled overnight, filtered and the filtrate evaporated to leave a light yellow solid. The solid was partitioned between 2M Na$_2$CO$_3$ (150 ml) and EA (3×150 ml) and the alkaline aqueous layer was then acidified (to pH1) with 2M hydrochloric acid and extracted with EA (3×300 ml). The latter extracts were combined, dried (MgSO$_4$) and evaporated to leave an off-white solid which on trituration with ER gave the title compound (0.3 g) as a white solid m.p. 102°–104°.

Intermediate 8

4-[2-(Dimethylamino)-2-oxoethyl]benzeneacetic acid

N,N'-Carbonyldiimidazole (11.4 g) was added to a stirred solution of 1,4-phenylenediacetic acid (11.4 g) in dry dimethylformamide (300 ml) under an atmosphere of nitrogen. The mixture was stirred at 20° for 2 h as dimethylamine gas (about 10 g) was bubbled through. The reaction mixture was then stirred at 20° for 3 h and evaporated in vacuo to leave a brown oil which was diluted with saturated K$_2$CO$_3$ solution (50 ml). The resulting mixture was evaporated in vacuo to leave an off-white solid which was triturated with EA (2×200 ml). The organic phase was discarded and the aqueous phase was acidified (pH1) with 5M hydrochloric acid to precipitate an off-white solid which was triturated with absolute ethanol (25 ml) and filtered to give the title compound (1.1 g) as a fine white solid m.p. 163°–165° (softening at 160°).

Intermediate 9

4-[[(methylsulphonyl)amino]methyl]benzeneacetic acid

A solution of ethyl 4-[[(methylsulphonyl)amino]methyl]benzeneacetate (3.1 g) and 1M KOH (22 ml) in ethanol (50 ml) was stirred at room temperature for 3 h and evaporated in vacuo to leave an off-white solid. This solid was dissolved in water (50 ml) and washed with EA (2×50 ml). The organic extract was discarded and the aqueous layer was acidified (pH1) with 5M hydrochloric acid (about 10 ml) to precipitate the title compound (2.54 g) as a white solid m.p. 167°–169°.

Intermediate 10

Methyl 4-[(2-propynylamino)carbonyl]benzoate

Terephthalic acid mono methyl ester (0.775 g) was dissolved in dry pyridine (10 ml) in a $N_2$ atmosphere. The solution was cooled in an ice-water bath, and thionyl chloride (0.44 ml) was added dropwise. The mixture was warmed to room temperature and was stirred for 1 h to give a pale brown suspension. The mixture was re-cooled in an ice-water bath, and a suspension of propargylamine hydrochloride (413 mg) in pyridine was added rapidly. The mixture was warmed to room temperature and was stirred for 18 h to give a dark solution. The solvent was evaporated in vacuo to give a dark brown gum, which was dissolved in Ea/hexane/acetic acid (1:1:1% v/v) and flash chromatographed using the same solvent system to give a yellow sludge, which was triturated with ER to give the title compound as a white solid, (0.544 g), m.p. 151.5°–153°.

Intermediate 11

Methyl 4-[[3-[3-[2-(dimethylamino)ethyl]-1H-indol-5-yl]-2-propynyl]amino]carbonyl]benzoate Intermediate 10 (1.0 g), 3-[2-(N,N-dimethylamino)ethyl]-5-iodo-1H-indole (0.35 g) and bis(triphenylphosphine)palladium dichloride (125 mg) were suspended in diethylamine (110 ml). Copper (I) iodide (67 mg) was added, and the mixture was stirred at room temperature for 24 h. The solvent was evaporated in vacuo to give a brown oil, which was slurried in $CH_2Cl_2$/ethanol/aqueous $NH_3$ (120:8:1) and flash chromatographed using the same solvent system to give a brown oil, which was triturated with ER to give a pale brown soild. The supernatant was treated with excess ER to give a pale brown solid. On cooling, the supernatant from the second crop gave a cream-coloured solid, which was dried in vacuo at 60° for 18 h, to yield the title compound (67 mg) m.p. 154.5°–156°.

Intermediate 12

Methyl 4-[[3-[3-[2-(dimethylamino)ethyl]-1H-indol-5-yl]propyl]amino]carbonyl]benzoate oxalate Intermediate 11 (1.25 g) was dissolved in methanol (100 ml) and activated charcoal (1 g) was added. The mixture was heated at reflux for 2 h, filtered and the filtrate added to a pre-reduced suspension of 10% palladium oxide-on-carbon (50% aqueous paste, 500 mg) in ethanol (20 ml). The resulting mixture was hydrogenated at 1 atmosphere hydrogen for 4 h then filtered and the filtrate was evaporated in vacuo to give a pale green oil. This oil was dissolved in (H) and flash chromatographed using the same solvent system to give the free base of the title compound as a white foam (590 mg). The white foam (99 mg) was dissolved in methanol (1 ml) and a solution of oxalic acid (21.5 mg) in methanol (0.5 ml) was added. The resulting solution was treated with ER (25 ml) to give a gummy precipitate. The mixture was stirred at room temperature for 4 h to give the title compound as a white solid, (75 mg), m.p. 98°–102° (becomes gummy), 138°–142° (clear oil).

Intermediate 13

4-[Methylsulphonyl)amino]benzenebutanoic acid

Methanesulphonyl chloride (2.26 ml) in $CHCl_3$ (30 ml) was added to a cooled (5°) solution of 4-aminobenzenebutanoic acid (3.5 g) in pyridine (35 ml) over a period of 30 min. After 1 h the solution was allowed to warm to room temperature and stirring continued overnight. The resulting solution was evaporated to a red oil. 2N hydrochloric acid (100 ml) was added and the resulting precipitate filtered off. The filtrate was extracted with EA (2×50 ml). The combined organic extracts and solid from filtration were evaporated to dryness in vacuo. Purification by flash chromatography [eluant ER] gave the title compound as a white solid (3 g) m.p. 108°–109°.

Intermediate 14

2-[3-[2-(Dimethylamino)ethyl]-1H-indol-5-yl]-N-methylethanamine, di-p-toluoyl-L-tartrate Intermediate 3 (3.0 g) was suspended in EA (150 ml) and saturated aqueous $K_2CO_3$ solution (100 ml) was added. Ethanol (50 ml) was added and the layers were separated. The aqueous layer was extracted with ethanol (100 ml) and the combined organic layers were evaporated in vacuo to given an aqueous sludge which was co-evaporated with toluene to give a dark brown oil. This oil was dissolved in a solution of methylamine in ethanol (33% w/w) (200 ml) and the solution was added to a pre-reduced suspension of 10% palladium oxide-on-carbon (50% aqueous paste, 3.0 g) in ethanol (75 ml). The mixture was hydrogenated at 1 atmosphere hydrogen for 72 h. The catalyst was removed by filtration through 'hyflo' and the filtrate was evaporated in vacuo to give a pale gum. This gum was dissolved in (C) and flash chromatographed using (C) grading to (25:8:1) to give the free base of the title compound (1.43 g) as a clear gum. A sample (90 mg) was dissolved in methanol (3 ml) and a solution of di-p-toluoyl-L-tartaric acid monohydrate (148 mg) in methanol (1 ml) was added. ER (45 ml) was added and the mixture was stirred at room temperature for 6 h to give the title compound (20 mg) as a white solid, m.g. 157°–160°.

Intermediate 15

4-Methoxy-N-[2-(4-nitrophenyl)ethyl]benzeneacetamide

A solution of 4-methoxybenzeneacetic acid (8.3 g) in dry THF (250 ml) was treated with triethylamine (6.9 ml) and wooled in a salt/ice-bath with stirring under a nitrogen atmosphere. Pivaloyl chloride (6.1 ml) was added and stirring continued for 1 h. A further aliquot of triethylamine (6.9 ml) was added followed by p-nitrophenethylamine hydrochloride (10 g). The resultant suspension was warmed to room temperature and stirred for 19.5 h (overnight). The reaction mixture was acidified to pH 1 using hydrochloric acid solution (2N; 30 ml) and the resultant solution was extracted with EA (1×250 ml, 1×100 ml). The combined organic extracts were washed with 8% $NaHCO_3$ solution (200 ml), dried ($MgSO_4$) and evaporated under reduced pressure to give a brown oil. Purification by 'flash' chromatography, ER:CH$_2$Cl$_2$ (4:1) gave the title compound as a pale yellow solid (7.4 g) m.p. 109°–110°.

Intermediate 16

N-[2-(4-aminophenyl)ethyl]-4-methoxybenzeneacetamide

A suspension of 10% PdO/C (500 mg of a 50% paste with H$_2$O) in absolute ethanol (50 ml) was stirred under one atmosphere of hydrogen at room temperature for 1 h. A solution of Intermediate 15 (1.5 g) in absolute ethanol (50 ml) was added and the mixture stirred for 2.5 h. The catalyst was removed by filtration and the filtrate evaporated under reduced pressure to give the title compound (1.3 g) as a white crystalline solid. A portion of the title compound was dried under vacuum at room temperature overnight to give a sample m.p. 112°–113.5°.

Intermediate 17

N-[2-(4-Hydrazinophenyl)ethyl]-4-methoxybenzeneacetamide hydrochloride

Sodium nitrite (0.122 g) in water (0.5 ml) was added to a stirred, cold (5°) suspension of Intermediate 16 (0.5 g) in a mixture of water (2 ml) and concentrated hydrochloric acid (6.5 ml). A further portion of water (4 ml) was added, the solution was filtered and the filtrate was poured into a stirred, cold (salt/ice bath) solution of tin (II) chloride dihydrate (1.99 g) in concentrated hydrochloric acid (5 ml). The resultant yellow suspension was filtered, the solid was collected and covered with ER and methanol (20 ml) added. The resultant homogeneous solution was evaporated under reduced pressure to give the title compound as a pale yellow foam (422 mg). T.l.c. (EA), Rf 0.14

Intermediate 18

N-[2-[4-[2-(3-Cyanopropylidene)hydrazino]phenyl]ethyl]-4-methoxybenzeneacetamide A suspension of Intermediate 17 (5.93 g) and 3-cyanopropionaldehyde diethyl acetal (3.23 ml) in water (200 ml) was treated with hydrochloric acid solution (2N; 2 ml) and stirred for 17 h at room temperature. The resultant white solid was filtered off, washed with water (50 ml) followed by ER (20 ml) then dried under vacuum at room temperature to give the title compound as a white powder. T.l.c. (EA) Rf 0.34.

Intermediate 19

N-[2-[3-(Cyanomethyl)-1H-indol-5-yl]ethyl]-4-methoxybenzeneacetamide

A solution of intermediate 18 (5.73 g) in polyphosphoric acid ethyl ester (57 g) and CHCl$_3$ (100 ml) was heated at reflux for 15 min and then poured onto ice (100 g). The resultant suspension was stirred for 20 min then the organic layer was separated and the aqueous layer was extracted with CHCl$_3$ (2×100 ml). The combined organic solutions were washed with NaHCO$_3$ solution (8%; 80 ml) and water (80 ml) then dried (MgSO$_4$) and evaporated in vacuo in the presence of silica gel. The impregnated silica was applied as a plug to a silica gel column (Merck Art 9385; 5 cm diam). Elution with EA-ER (1:1) followed by EA-ER-ethanol (9:9:2) gave the title compound as a pale yellow solid (60 mg) m.p. 155°–156°.

Intermediate 20

4-(Acetylamino)-N-[2-[3-[2-(1,3-dihydro-1,3-dioxo-2H-isoindol-2-yl)-ethyl]-1H-indol-5-yl]ethyl]benzeneacetamide Triethylamine (222 mg) was added to a solution of 4-(acetylamino)benzeneacetic acid (386 mg) in dry THF (12 ml) at 5° (ice bath) under nitrogen. Pivaloyl chloride (265 mg) was then added. The mixture was stirred in an ice bath for 1 h. Solid 2-[2-[5-(2-aminoethyl)-1H-indol-3-yl]-1H-isoindole-1,3-(2H)-dione, hydrochloride (615 mg) was added to the resultant white suspension, followed immediately by triethylamine (222 mg). The mixture was stirred at 21° for 4 h then partitioned between 2N hydrochloric acid (20 ml) and EA (30 ml). The organic phase was separated, washed with 2N hydrochloric acid (20 ml), water (20 ml), 8% NaHCO$_3$ solution (2×10 ml), water (20 ml) and saturated brine (20 ml), dried (Na$_2$SO$_4$) and evaporated to give an oil. The oil was chromatographed using initially EA and then a mixture of EA and methanol (100:1), to give the title compound (275 mg) as a yellow foam. Solidification gave a yellow powder (m.p. 191°–195°).

In the following Examples, Intermediate 4 was used as the free base.

EXAMPLE 1

N-[2-[3-[2-(Dimethylamino)ethyl]-1H-indol-5-yl]ethyl]-4-methoxybenzeneacetamide oxalate N,N'-carbonyldiimidazole (195 mg) was added to a stirred solution of 4-methoxyphenylacetic acid (166 mg) in dry CH$_2$Cl$_2$ (10 ml) at room temperature under nitrogen, and stirring was continued for 1 h. Intermediate 4, (231 mg) was added in CH$_2$Cl$_2$ (10 ml), and stirring was continued for 1 h. The reaction mixture was combined with a similarly-prepared mixture, washed with 8% aqueous NaHCO$_3$ (20 ml) and water 2×20 ml), dried (MgSO$_4$) and evaporated to give an oil (0.723 g). Purification by flash chromatography (B) gave an oil (214 mg; first crop) and slightly impure material (119 mg; second crop). The first crop was dissolved in methanol (2 ml), and oxalic acid (56 mg) in methanol (1 ml) was added. Addition of dry ER gave a precipitate which was filtered off, washed with dry ER and dried to give the title salt as a solid (0.274 g) m.p. ca 96°–103° (foams).

N.m.r. δ(DMSO) includes 2.68 (6H, s, NMe$_2$); 3.25–3.36 (4H, m, CONHCH$_2$CH$_2$ and COCH$_2$Ar); 3.73 (3H, s, OCH$_3$); 8.10 (1H, t, CONH); and 10.9 (1H, brs, indole, NH).

EXAMPLE 2

4-(Acetylamino)-N-[2-[3-[2-(dimethylamino)ethyl]-1H-indol-5-yl]ethyl]benzeneacetamide oxalate A mixture of N,N'-carbonyldiimidazole (0.81 g) and 4-(acetylamino)benzeneacetic acid (0.97 g) in dry THF (75 ml) was stirred under nitrogen at reflux for 1.5 h and then Intermediate 4 (1.2 g) was added. Refluxing was continued for 5 h and the mixture was allowed to cool to room temperature and concentrated in vacuo to leave a gum (ca. 3 g) which was purified by flash chromatography (C) and appropriate fractions were combined and evaporated. The resulting gum (0.7 g) was dissolved in absolute ethanol (70 ml) and treated with ethereal hydrogen chloride until the solution was acidic. The resulting solution was diluted with dry ER (120 ml) to precipitate a solid which was triturated with fresh dry ER (120 ml×2) to give the title compound, hydrochloride salt (0.4 g) as a white solid. The salt was converted to the title compound, free base on a column of silica (C). The free base obtained (0.33 g) was dissolved in absolute ethanol (35 ml) and treated with a solution of oxalic acid (0.07 g) in ethanol (15 ml). The resulting solution was diluted with dry ER (120 ml) to precipitate the title compound (0.33 g) as a solid, m.p. (softens) 75°–80°, (foams) 115°–120°.

N.m.r. δ(DMSO) includes 2.05 (3H, s, COC$\underline{H}_3$); 2.7–2.865 (8H, m, NM$\underline{e}_2$ and ArC$\underline{H}_2$CH$_2$NHCO); 8.13 (1H, t, CONH$\underline{C}$H$_2$); 10.0 (1H, s, N$\underline{H}$COCH$_3$) and 10.95 (1H, brs, indole N$\underline{H}$).

EXAMPLE 3

N-[2-[3-[2-(Dimethylamino)ethyl]-1$\underline{H}$-indol-5-yl]ethyl]-1,4-benzene diacetamide d,l-tartrate compound with water A mixture of N,N'-carbonyldiimidazole (0.37 g) and 4-(aminocarbonylmethyl)benzene acetic acid (0.45 g) in dry distilled THF (150 ml) was stirred under nitrogen at reflux for 1.5 h and then Intermediate 4, (0.54 g) was added. Refluxing was continued for 3 h and the mixture was allowed to cool to room temperature. The cooled mixture was evaporated in vacuo to leave a gum (ca 2 g) which was adsorbed onto silica and purified by flash chromatography (C). Appropriate fractions were combined and evaporated to leave a solid (0.43 g) which was adsorbed onto alumina (Merck 1077) and chromatographed on alumina (E) to effect further purification. Appropriate fractions were combined and evaporated to leave a solid (0.28 g) which was dissolved in hot absolute ethanol (3 ml) and treated with a hot solution of tartaric acid (0.1 g). The resulting solution was diluted with dry ER (50 ml) to precipitate a solid which was stirred under ER at 20° for 24 h and filtered to give the title compound (0.38 g) as a solid m.p. (shrinks) 68°–72° (foams) 80°–82°.

N.m.r. δ(DMSO) includes 2.65–2.75 (8H, m, NM$\underline{e}_2$ and ArC$\underline{H}_2$CH$_2$NHCO); 3.28–3.40 (6H, m, ArC$\underline{H}_2$CONH$_2$ and ArC$\underline{H}_2$CONHCH$_2$); 8.15 (1H, t, CONH$\underline{C}$H$_2$) and 10.88 (1H, d, indole N$\underline{H}$).

EXAMPLE 4

4-Chloro-N-[2-[3-[2-(dimethylamino)ethyl]-1$\underline{H}$-indol-5-yl]ethyl]benzeneacetamide hydrochloride compound with water A mixture of N,N'-carbonyldiimidazole (0.58 g) and 4-chlorobenzene acetic acid (0.61 g) in dry THF (75 ml) was stirred under nitrogen at reflux for 2 h and then Intermediate 4 (0.7 g) was added. Refluxing was continued for 3 h and the mixture was allowed to cool to room temperature. The cooled mixture was evaporated in vacuo to leave a semi-solid (20 g) which was purified by flash chromatography (C). Appropriate fractions were combined and evaporated to leave a solid (0.9 g) which was partitioned between CH$_2$Cl$_2$ (3×100 ml) and H$_2$O (100 ml). The organic extracts were combined, washed with H$_2$O (100 ml), dried (Na$_2$SO$_4$) and evaporated. The resulting gum (0.7 g) was dissolved in absolute ethanol (15 ml) and treated with ethereal hydrogen chloride (2ml) to give a cloudy solution which was diluted with dry ER (50 ml) to precipitate a solid. The supernatant liquid was decanted and the solid triturated with fresh ER (100 ml) to give the title compound (0.63 g) as a solid m.p. (softens) 65°–7°, (melts) 95°–100°.

N.m.r. δ(DMSO) includes 2.7–2.85 (8H, m, NM$\underline{e}_2$ and ArC$\underline{H}_2$CH$_2$NHCO); 3.3–3.5 (4H, m, ArC$\underline{H}_2$CONHCH$_2$); 8.27 (1H, t, CONH$\underline{C}$H$_2$) and 1095 (1H, brd, indole N$\underline{H}$).

EXAMPLE 5

4-(Aminocarbonyl)-N-[2-[3-[2-(dimethylamino)ethyl]-1$\underline{H}$-indol-5-yl]-ethyl]benzeneacetamide, hydrochloride compound with water and ethanol A suspension of N,N'-carbonyldiimidazole (0.58 g) and Intermediate 5 (0.59 g) in dry THF (20 ml) under nitrogen was refluxed for 2 h and then Intermediate 4 (0.7 g) was added. Refluxing was continued for a further 17 h and the cooled mixture evaporated in vacuo to give a brown gum which was purified by flash chromatography (F). The second fraction (100 ml) (first=300 ml) was collected and evaporated to leave a light brown gum which was crystallised from a mixture of ethanol (20 ml) and ER (20 ml) to give a white solid which was dissolved in warm ethanol (30 ml) and treated with ethereal hydrogen chloride (2 ml). The resulting solution was stirred under nitrogen for 0.5 h, then diluted with ER (100 ml) to precipitate a white solid. The supernatant was decanted and the solid triturated with ER (100 ml) to give title compound (0.26 g) as a white solid m.p. (softens) 65°–70° (melts) 120°–124°.

EXAMPLE 6

N-[2-[3-[2-(Dimethylamino)ethyl]-1$\underline{H}$-indol-5-yl]ethyl]-4-[(methylsulphonyl)amino]benzenemethanesulphonamide hydrochloride compound with ethanol A solution of Intermediate 6 (0.68 g) and Intermediate 4 (1.4 g) in pyridine (6 ml) was heated at 100° for 2 h. The resulting mixture was evaporated to leave a brown gum which was adsorbed on silica and purified by flash chromatography (C) collecting 50 ml fractions. Fractions 28–32 were combined and evaporated to leave a pale brown foam which was dissolved in absolute ethanol (26 ml) and treated with ethereal hydrogen chloride and ER (30 ml) to precipitate the title compound (0.24 g) as an off-white solid m.p. (shrinks) 120°–125°, (foams) 135°–140°.

EXAMPLE 7

N-[2-[3-[2-(Dimethylamino)ethyl]-1$\underline{H}$-indol-5-yl]ethyl]-4-[(methylsulphonyl)amino]benzeneacetamide oxalate compound with water A mixture of N,N'-carbonyldiimidazole (1.62 g) and 4-[(methylsulphonyl)amino]benzeneacetic acid (2.3 g) in dry distilled THF (100 ml) was stirred under nitrogen at reflux for 2.5 h and then Intermediate 4 (1.2 g) was added. Refluxing was continued for 4 h and the mixture allowed to cool to 20° overnight. The cooled mixture was evaporated in vacuo to leave a brown gum which was partitioned between EA (3×100 ml) and 2M hydrochloric acid (100 ml). The acidic aqueous layer was basified (to pH 8) with $K_2CO_3$ and extracted with EA (3×150 ml). The EA extracts were combined and washed with brine (3×150 ml), dried ($Na_2SO_4$) and evaporated to leave a brown gum, which was purified by flash chromatography (C) collecting 25 ml fractions. Fractions 26–32 were combined and evaporated to leave a white foam which was dissolved in hot ethanol (150 ml) and treated with a hot solution of oxalic acid (0.25 g) in ethanol (65 ml) to precipitate on cooling (0°), the title compound (1.17 g) as white solid m.p. 165°–166°.

EXAMPLE 8

4-(Acetylamino)-N-[2-[3-[2-(dimethylamino)ethyl]-1H-indol-5-yl]ethyl]benzeneacetamide oxalate Oxalyl chloride (1.1 ml) was added dropwise to a cold (0°) stirred suspension of 4-(acetylamino)benzeneacetic acid (1.6 g), in dry $CH_2Cl_2$ (80 ml) under nitrogen. The resulting mixture was allowed to warm to room temperature and stirred and 3 h, a further quantity of oxalyl chloride (1.1 ml) was added and the mixture stirred at 20° for a further 3 h. The mixture was then evaporated in vacuo below 30° to leave a yellow solid which was dissolved in dry THF (80 ml) and added to a stirred solution of triethylamine (2.5 ml) and Intermediate 4 (1.27 g) in dry THF (80 ml). The resulting yellow mixture was stirred at 20° for about 19 h, diluted with methanol (20 ml) and evaporated in vacuo to leave a brown solid (about 3.0 g). This was purified by flash chromatography (G) to give a brown gum which was further purified by column chromatography eluting with methanol:ammonia (100:1) to give the title compound, free base as a colourless foam. Part of the foam (0.21 g) was dissolved in warm ethanol (5 ml) and treated with oxalic acid (47 mg) in ethanol (2 ml) to precipitate the title compound (0.18 g) as a white solid m.p 201°–202° (foams).

EXAMPLE 9

4-(Acetylamino)-N-[2-[3-[2-(dimethylamino)ethyl]-1H-indol-5-yl]ethyl]benzeneacetamide oxalate compound with water and ethanol A suspension of 4-(acetylamino)benzeneacetic acid (0.083 g) in dry $CH_2Cl_2$ (20 ml) was treated with trimethylacetyl chloride (0.06 ml) followed by triethylamine (0.12 ml). The reaction mixture was stirred at 20° for 2 h to give a clear solution to which a solution of Intermediate 4 (0.1 g) in dry $CH_2Cl_2$ (20 ml) was added. The resulting mixture was stirred at 20° for 20 h and evaporated in vacuo to leave a brown gum which was purified by column chromatography (I) to give an off-white foam which was dissolved in absolute ethanol (5 ml) to precipitate the title compound (80 mg) as a white solid m.p. 201°–202° (foams).

EXAMPLE 10

4-(Acetylamino)-N-[2-[3-[2-(dimethylamino)ethyl]-1H-indol-5-yl]ethyl]benzeneacetamide oxalate compound with water and ethanol A suspension of 4-(acetylamino)benzeneacetic acid (0.083 g) and Intermediate 5 (0.1 g) in dry $CH_2Cl_2$ (40 ml), at 5° was treated with triethylamine (0.12 ml) followed by diphenylphosphorylazide (0.185 ml). The resultant suspension was stirred at room temperature for 21 h and evaporated in vacuo to leave a yellow gum which was partitioned between EA (3×35 ml) and 0.2M hydrochloric acid (35 ml). The organic phase was discarded and the acidic aqueous phase was basified (pH 8) with $K_2CO_3$ and extracted with EA (3×35 ml). This organic extract was dried ($Na_2SO_4$) and evaporated to leave an off-white foam which was purified by column chromatography (I) to give a white foam which was dissolved in absolute ethanol (5 ml) and treated with oxalic acid (27 mg) in ethanol (5 ml) to precipitate the title compound (80 mg) as a white solid m.p. 200.5°–202° (foams).

EXAMPLE 11

N-[2-[3-[2-(Dimethylamino)ethyl]-1H-indol-5-yl]ethyl]-4-[[(methylsulphonyl)amino]methyl]benzeneacetamide oxalate compound with water A suspension of Intermediate 9 (0.73 g) and Intermediate 4 (0.7 ) in dry $CH_2Cl_2$ (240 ml) under nitrogen at 5° was treated with triethylamine (0.9 ml) followed by diphenylphosphorylazide (1.29 ml). The resultant suspension was stirred at room temperature for 21 h and quenched with 1M hydrochloric acid (2×75 ml). The two phases were separated, the organic phase was discarded and the acidic aqueous layer was further washed with EA (75 ml). The acidic aqueous layer was basified (pH8) with $K_2CO_3$ and extracted with a mixture of EA:isopropanol (20:1, 3×100 ml). These organic extracts were combined, washed with brine (100 ml), dried ($Na_2SO_4$) and evaporated to leave a white foam which was purified by flash chromatography (I) to give a white foam which was dissolved in absolute ethanol (70 ml) and treated with oxalic acid (0.138 g) in ethanol (5 ml) to precipitate the title compound (0.58 g) as a white solid m.p. 168°–169°.

EXAMPLE 12

N-[3-[3-[2-(dimethylamino)ethyl]-1H-indol-5-yl]propyl]amino-1,4-benzeneacetamide oxalate compound with water Intermediate 12 (476 mg) was dissolved in methanolic ammonia (3.1M, 30 ml) and further ammonia was bubbled through the solution for about 5 min. The mixture was heated at 110° for 72 h. The solvent was evaporated in vacuo to give a pale brown foam, which was dissolved in $CH_2Cl_2$/ethanol/$NH_3$(aqueous) and flash chromatographed using the same solvent system to give the free base of the title compound as a white solid (381 mg). The free base (369 mg) was dissolved in methanol (3 ml) and a solution of oxalic acid (84 mg) in methanol (1 ml) was added. ER (75 ml) was added, and the mixture was stirred at room temperature for 6 h, resulting in the formation of a white precipitate. The title compound was isolated by filtration, (435 mg), m.p. 150°–155° C.

EXAMPLE 13

4-(Aminosulphonyl)-N-[2-[3-[2-(dimethylamino)ethyl]-1H-indol-5-yl]ethyl]benzeneacetamide oxalate compound with water and ethyl acetate A mixture of 4-(aminosulphonyl)benzeneacetic acid (0.58 g) and Intermediate 4 (0.56 g) in dry CH$_2$Cl$_2$ (150 ml) under nitrogen at 5° was treated with triethylamine (0.7 ml) followed by diphenylphosphorylazide (1 ml). The resultant suspension was stirred at room temperature for 24 h and quenched with 1M hydrochloric acid (2×60 ml). The organic phase was discarded and the aqueous layer was washed with EA (60 ml), then basified (pH8) with K$_2$CO$_3$ and extracted with a mixture of EA:isopropanol (20:1, 3×100 ml). The organic extracts were combined, washed with brine (100 ml), dried (Na$_2$SO$_4$) and evaporated to leave an off-white foam, which was purified by column chromatography (I) to give a white foam which was dissolved in hot ethanol (25 ml) and treated with oxalic acid (0.14 g) in ethanol (10 ml). The resulting solution was cooled to about 20° and diluted with dry EA (about 100 ml) to precipitate the title compound (0.56 g) as an off-white solid m.p. (shrinks) 123°–125°.

EXAMPLE 14

4-[(Acetylamino)methyl]-N-[2-[3-[2-(dimethylamino)ethyl]-1H-indol-5-yl]ethyl]benzeneacetamide d,l-tartrate compound with water A suspension of 4-[(acetylamino)methyl]benzene acetic acid (0.62 g) and Intermediate 4 (0.7 g) in dry CH$_2$Cl$_2$ (240 ml) under nitrogen at 5° was treated with triethylamine (0.9 ml) followed by diphenylphosphorylazide (1.29 ml). The resultant suspension was stirred at room temperature for 64 h and quenched with 1M hydrochloric acid (2×75 ml). The two phases were separated, the organic phase discarded, and the aqueous layer was washed with EA (75 ml). The EA extract was discarded and the acidic aqueous layer was basified (pH8) with K$_2$CO$_3$ and extracted with a mixture of EA:isopropanol (20:1, 3×100 ml). The organic extracts were combined, washed with brine (100 ml), dried (Na$_2$SO$_4$) and evaporated to leave a brown gum which was purified by column chromatography (I) to leave a pale brown foam which was dissolved in absolute ethanol (15 ml) and treated with oxalic acid (90 mg) in ethanol (10 ml). The resulting solution was diluted with dry ER (about 100 ml) to precipitate an off-white solid which formed a gum on filtration. This gum was dissolved in water (20 ml) and dilute hydrochloric acid (2M, 2 ml) and the aqueous solution was washed with EA (2×20 ml). The organic washings were discarded and the aqueous layer was basified with K$_2$CO$_3$ and extracted with a mixture of EA and isopropanol (20:1, 3×50 ml). The organic extracts were combined, dried (Na$_2$SO$_4$) and evaporated in vacuo to leave a pale brown gum (0.35 g) which was dissolved in absolute ethanol (20 ml) and treated with a hot solution of d,l-tartaric acid (125 mg) in ethanol (10 ml). The resulting solution was diluted with dry ER to precipitate on off-white solid. This solid was filtered and dried to give the title compound (0.29 g) as a pale brown solid m.p. (shrinks) 90°–93° (foams) 95°–100°.

EXAMPLE 15

N-[2-[3-[2-(Dimethylamino)ethyl]-1H-indol-5-yl]ethyl-N$^1$,N$^1$-dimethyl-1,4-benzenediacetamide d,l-tartrate compound with water A suspension of 4-[2-(dimethylamino)-2-oxoethyl]-benzeneacetic acid (0.74 g) and Intermediate 4 (0.7 g) in dry CH$_2$Cl$_2$ (300 ml) under nitrogen at 5° was treated with triethylamine (1 ml) followed by diphenylphosphorylazide (1.29 ml). The resultant suspension was stirred at room temperature for 60 h and quenched with 1M hydrochloric acid (2×75 ml). The two phases were separated, the organic phase was discarded and the acidic aqueous layer was further washed with EA (75 ml). The organic extract was discarded and the aqueous fraction was basified (pH8) with K$_2$CO$_3$ and extracted with a mixture of EA:isopropanol (20:1, 3×100 ml). The organic extracts were combined, washed with brine (100 ml), dried (Na$_2$SO$_4$) and evaporated to leave a white foam which was purified by column chromatography (I) to give a white foam which was dissolved in hot absolute ethanol (65 ml) and treated with tartaric acid (215 mg) in ethanol (15 ml). The resulting solution was cooled to 20° and diluted with dry EA (about 200 ml) to precipitate the title compound (0.65 g) as a white solid m.p. (shrinks) 85°–90° (foams) 100°–110°.

EXAMPLE 16

(a)

N-[2-[3-[2-(Dimethylamino)ethyl]-1H-indol-5-yl]ethyl]-4-methoxybenzene propanamide oxalate Diphenylphosphorylazide (1.5 ml) was added to a solution of Intermediate 4 (0.8 g) and 3-(4-methoxyphenyl)propanoic acid (0.62 g) in THF (100 ml) and triethylamine (0.96 ml) and stirred at 5° for 1.5 h. The solution was allowed to warm up to room temperature and stirred for an extra 16 h. The resulting solution was added to saturated NH$_4$Cl (100 ml) and extracted with EA (3×50 ml). The combined organic extracts were dried (Na$_2$SO$_4$) and evaporated in vacuo to give the crude product as a clear oil. Purification by flash chromatography (H) gave pure title compound free base as a clear oil (1.0 g). The free base was dissolved in hot ethanol (10 ml) and oxalic acid (0.25 g) in ethanol (2 ml) was added, the solution was evaporated to dryness and the resulting solid recrystallised from CHCl$_3$ (20 ml) and ethanol (3ml) to give the title compound as a white solid (0.6 g) m.p. 112°–114°.

The following compounds were prepared in a similar manner:

(b) N-[2-[3-[2-(Dimethylamino)ethyl]-1H-indol-5-yl]ethyl]-3-[4-[(methylsulphonyl)amino]benzene propanamide oxalate compound with water, (0.36 g) m.p. 83°–85°, from Intermediate 4 (0.8 g) and 4-[(methylsulphonyl)amino]-benzenepropanoic acid (0.72 g).

(c) 4-(Acetylamino)-N-[2-[3-[2-(dimethylamino)ethyl]-1H-indol-5-yl]-ethyl]benzenepropanamide oxalate compound with water, (0.35 g) m.p. 161°–162°, from Intermediate 4 (0.8 g) and 4-(acetylamino)benzenepropanoic acid (0.72 g).

(d) N-[2-[3-[2'-(Dimethylamino)ethyl]-1H-indol-5-yl]ethyl]-4-[(methylsulphonyl)amino]benzenebutanamide oxalate, (1 g) m.p 70°-75° from Intermediate 4 (0.8 g) and Intermediate 13 (0.8 g).

EXAMPLE 17

N-[2-[3-[2-(Dimethylamino)ethyl]-1H-indol-5-yl]ethyl]-N¹methyl-1,4-benzenediacetamide d,l tartrate compound with water and ethyl acetate A suspension of Intermediate 7 (0.21 g) and Intermediate 4 (0.23 g) in dry $CH_2Cl_2$ (80 ml) under nitrogen at 5° was treated with triethylamine (0.3 ml) followed by diphenylphosphorylazide (0.43 ml). The resultant suspension was stirred at room temperature for 23 h and extracted into 1M hydrochloric acid (2×320 ml). The acidic aqueous layers were combined and washed with EA (40 ml), basified (pH8) with $K_2CO_3$ and extracted with EA:isopropanol (20:1, 3×30 ml). The organic extracts were combined, washed with brine (30 ml), dried ($Na_2SO_4$) and evaporated to leave a brown gum which was purified by flash chromatography (I) to give a white foam which was dissolved in hot absolute ethanol (20 ml) and treated with d,l tartaric acid (0.068 g) in hot ethanol (5 ml). The resulting solution was cooled (20°) and diluted with dry EA (about 150 ml) to precipitate the title compound (0.2 g) as an off-white solid m.p. 85°-90° (foams).

EXAMPLE 18

4-Acetylamino)-N-[2-[3-[2-(dimethylamino)ethyl]-1H-indol-5-yl]ethyl]benzenebutanamide succinate Diphenylphosphoryl azide (1.5 ml) was added to a cooled (ice bath) solution of Intermediate 4 (0.8 g) and 4-(acetylamino)benzenebutanoic acid (0.76 g) in THF (100 ml) and triethylamine (1 ml). After 1 h the solution was allowed to warm to room temperature and stirring continued overnight. Saturated $K_2CO_3$ (100 ml) was added and the solution extracted with ethanol (2×50 ml). The combined organic extracts were evaporated to dryness in vacuo to give a brown oil which was purified by chromatography (C) to give the title compound, free base as a brown oil (0.6 g). The free base (0.6 g) was dissolved in hot $CHCl_3$/ethanol (10:1) (20 ml) and succinic acid (0.17 g) in ethanol (2 ml) was added and on cooling the title compound crystallised out as a light brown solid (0.3 g) m.p. 68°-70°.

EXAMPLE 19

N-(Acetylamino)-N-[[2-[3-[2-(dimethylamino)ethyl]-1H-indol-5-yl]ethyl]methylamino]benzeneacetamide oxalate compound with water 4-Acetylamino)benzeneacetic acid (696 mg) was dissolved in dry dimethylformamide (30 ml) containing triethylamine (0.56 ml) in a nitrogen atmosphere. The solution was cooled in an ice-bath and pivaloyl chloride (0.50 ml) was added. The mixture was stirred in the ice-bath for 1 h to give a white precipitate, and a solution of Intermediate 14, free base (868 mg) in dimethylformamide (20 ml) was added dropwise. The resulting suspension was stirred at room temperature for 72 h. The solvent was evaporated in vacuo to give an oil which was suspended in (C) and flash chromatographed (C) to give the free base of the title compound (1.11 g) as a clear gum.

A sample (892 mg) was dissolved in methanol (3 ml) and oxalic acid (182 mg) was added. The resulting solution was treated with ER (80 ml) and the mixture was stirred for 6 h to give the title compound (1.01 g) as a white solid, m.p. (foams) 100°-110°.

EXAMPLE 20

N-[2-[3-(2-Aminoethyl)-1H-indol-5yl]ethyl]-4-methoxybenzeneacetamide oxalate compound with water and butanol A mixture of Intermediate 17 (500 mg), $Na_2HPO_4$ (21 mg) and 4-chlorobutanol sodium bisulphite addition complex (89% w/w; 156 mg) in water (25 ml) and ethanol (50 ml) was heated at reflux under a nitrogen atmosphere for 26 h. Solid $K_2CO_3$ was added to the solution until 2 layers were observed. The organic layer was separated and the aqueous layer extracted with ethanol (20 ml). The combined organic solutions were evaporated in vacuo to give a solid which was purified by flash chromatography (C) to give the free base of the title compound (175 mg). A solution of oxalic acid (42.9 mg) in ethanol (0.5 ml) was added to a solution of the free base (172 mg) in ethanol (2 ml). The resultant gum was stirred with ER until a fine solid was formed, which was filtered off and dried under vacuum at room temperature for 2 h, to afford the title compound as a salmon pink solid (190 mg) m.p. 43°-45° (foams).

EXAMPLE 21

(a)

N-[2-[3-[2-(Methylamino)ethyl]-1H-indol-5-yl]ethyl]-4-methoxybenzeneactamine oxalate Intermediate 19 (800 mg) in ethanolic methylamine (33% w/w; 50 ml) was hydrogenated over pre-reduced 10% PdO/C (1 g of a 50% paste with water) in absolute ethanol (20 ml) under one atmosphere of hydrogen at room temperature for 68 h. The catalyst was removed by filtration and the filtrate evaporated in vacuo to give a pale yellow foam. Purification by 'flash' chromatography (C) gave the free base of the title compound (672 mg). A solution of oxalic acid (157 mg) in ethanol (1 ml) was added to a solution of the free base (637 mg) in ethanol (3 ml). The supernatant liquid was decanted from the resultant gum and replaced with ER (50 ml). After stirring with ER for 2 h the gm solidified. The solid was filtered off and dried under vacuum at room temperature for 26 h to afford the title compound as a white, crystalline solid (676 mg) m.p. 157°-159°.

(b) N-[2-[3-[2-(Ethylamino)ethyl]-1H-indol-5-yl]ethyl]-4-methoxybenzeneacetamide oxalate (753 mg) m.p. 88°-90° (glass) was prepared in a similar manner from Intermediate 19 (800 mg) in ethanolic ethylamine (33% w/w; 50 ml).

EXAMPLE 22

4-(Acetylamino-N-[2-[3-(2-aminoethyl)-1H-indol-5-yl]ethyl]benzeneacetamide hemi-succinate compound with water A solution of Intermediate 20 (787 mg) and hydrazine hydrate (1.01 ml) in absolute ethanol (60 ml) was stirred and heated at reflux for 4 h; cooled and evaporated. The residue was partitioned between EA (60 ml) and 2N $Na_2CO_3$ (40 ml). The aqueous phase was separated and extracted with EA (3×50 ml). The combined organics were dried ($Na_2SO_4$) and evaporated to give a gum which was chromatographed using $C_2Cl_2$, ethanol and ammonia (20:8:1) as the eluent, to give the title compound, free base as a colourless gum. The gum was dissolved in a hot mixture of EA (10 ml) and ethanol (20 ml). A solution of succinic acid (150 mg) in hot ethanol (1 ml) was added. A white powder was immediately deposited. The mixture was left at 0° overnight, then filtered. The solid residue was dried in vacuo to give the title compound (307 mg) as a white powder, m.p. 212°-214°.

EXAMPLES 23-30

These illustrate the preparation of 4-(acetylamino)-N-[2-[3-[2-(dimethylamino)ethyl]-1H-indol-5-yl]ethyl]benzeneacetamide, (referred to as the title product). In each instance where the presence of the compound was determined by h.p.l.c. analysis this was carried out against an authentic sample with a 5μ-ODS 1 column eluting with $CH_3CN(68):H_2O$ (20):0.05M sodium acetate adjusted to pH5 with 6% acetic acid (12); flow 3 ml/min. Yields quoted are % of theory.

EXAMPLE 23

A solution of triphenylphosphite (1.6 g) and triethylamine (0.72 ml), in dry dimethylformamide (40 ml) was stirred at 20° for 5 min. A solution of 4-acetylaminobenzeneacetic acid (1 g) in dry dimethylformamide (10 ml) was added and the stirring continued for 15 min. The resulting mixture was treated with a suspension of Intermediate 4 (1.32 g), and triethylamine (1.2 ml) in dry dimethylformamide (20 ml) and the solution was stirred at 40°, under nitrogen, for 20 h to yield the title product (h.p.l.c.—68%).

EXAMPLE 24

A solution of 1,3-dicyclohexyl-carbodiimide (1.34 g) in $CH_2Cl_2$ (10 ml) was treated with a solution of 4-acetylaminobenzeneacetic acid (1.25 g) in dimethylformamide (5 ml) and dichloromethanae (5 ml) over 5 min at 0°-5°. The resulting suspension was stirred for 10 min at 0° and treated with a suspension of Intermediate 4 (1.32 g) and triethylamine (1.25 ml) in dry dimethylformamide (15 ml) over 5 min at 0°-5°. The solution was allowed to warm to room temperature and stirred under nitrogen for 18 h to yield the title product (h.p.l.c.—62%).

EXAMPLE 25

A solution of oxalyl chloride (0.471 ml) in $CH_2Cl_2$ (10 ml) was added to a mixture of dimethylformamide (10 ml) and $CH_2Cl_2$ (10 ml) at $-10°$ to $-15°$. After stirring for a further 20 min at $-6°$ to $-10°$, a solution of 4-acetylaminobenzeneacetic acid (958 mg) in dimethylformamide (10 ml) was added while maintaining the reaction mixture below $-2°$. The resulting suspension was stirred at 0° for 30 min, cooled to $-15°$ and then treated with a solution of Intermediate 4 (1.2 g) and triethylamine (2.23 ml) in dry dimethylformamide (10 ml) over 5 min. The mixture was then slowly allowed to warm to 20° and stirred for 1 h to yield the title product (h.p.l.c.—71%).

EXAMPLE 26

A solution of 4-acetylaminobenzeneacetic acid (1.00 g) Intermediate 4 (1.32 g), triphenylphosphine (2.02 g) and triethylamine (3.29 ml) in a mixture of dry dimethylformamide (32 ml) and $CH_2Cl_2$ (22 ml) was treated dropwise at 0°-5° C. with a solution of $CCl_4$(7.26 ml) in $CH_2Cl_2$ (10 ml) over about 20 min. The resulting mixture was stirred at room temperature under nitrogen for 20 h to yield the title product (h.p.l.c.—59.6%).

EXAMPLE 27

A stirred solution of the compound of Example 22 (175 mg) in methanol (2 ml) was treated portionwise with 0.05 ml aliquots of (a) 0.35 ml 40% HCHO in 0.35 ml methanol and (b) 0.1 g $NaBH_4$ in 1 ml $H_2O$. The additions were carried out at 5°-10° (ice bath), with (a) being added before (b). The reaction mixture was monitored by t.l.c. following each addition of (a) and (b). When all the starting material had been consumed, the reaction mixture was warmed to 21° over 1 h then evaporated to give a gum. The material was chromatographed using a mixture of $CH_2Cl_2$, ethanol and ammonia (40:8:1) as the eluent, to give the title product (101 mg) as a white foam. T.l.c (C) Rf 0.25.

EXAMPLE 28

A suspension of 4-(acetylamino)benzeneacetic acid (1.00 g) in dry $CH_2Cl_2$ (50 ml) was treated with trimethylacetyl chloride (0.72 ml) followed by triethylamine (1.44 ml), and the mixture was stirred at room temperature under nitrogen for 2.3 h, when an amber solution was obtained. A solution of Intermediate 4 (1.32 g), and triethylamine (1.20 ml) in dry dimethylformamide (50 ml) was added, and the solution was stirred at room temperature under nitrogen for 20.7 h to yield the title product (h.p.l.c.—43.7%).

EXAMPLE 29

(a) 4-(Acetylamino)benzene N-[2-(4-nitrophenyl)ethyl]acetamide 4-(Acetylamino)benzeneacetic acid (3.42 g) was dissolved in tetrahydrofuran (150 ml) and the solution was cooled in an ice bath. Triethylamine (2.71 ml) was added, followed by pivaloyl chloride (2.4 ml). The mixture was stirred in the ice bath for 1 h to give a white precipitate. Further triethylamine (2.71 ml) was added, followed by the solid 4-nitrophenethylamine hydrochloride (3.59 g) and the mixture was stirred at room temperature for 20 h. The reaction mixture was poured into saturated aqueous $NaHCO_3$ solution (200 ml) and the aqueous layer was extracted with EA (2×200 ml). The combined organic layers were dried $MgSO_4$ and evaporated in vacuo to give an orange solid which was suspended in CH$_2$Cl$_2$/ethanol/aqueous NH$_3$ (200:8:1) and flash chromatographed using the same solvent system, grading to (C) to give the title compound which was recrystallised from ethanol as pale orange needles (1.06 g), m.p. 197°–200°.

(b) 4-Acetylamino N-[2-(4-aminophenyl)ethyl]benzeneacetamide, dihydrochloride The compound of Section (a) (0.881 g) was dissolved in ethanol (150 ml) and saturated ethanolic hydrogen chloride (15 ml). The resulting solution was added to a pre-reduced suspension of 10% palladium oxide-on-carbon (0.5 g, dry) in ethanol (50 ml). The mixture was hydrogenated at 1 atmosphere hydrogen for 2 h (hydrogen uptake ceased). The catalyst was removed by filtration through 'hyflo' and the filtrate was evaporated in vacuo to give a brownish gum which was triturated with ER (2×200 ml) and flash chromatographed (C) to give the free base of the title compound as a pale gum. This gum was dissolved in saturated ethanolic hydrogen chloride and the solution was evaporated in vacuo to give a gummy solid which was triturated with ER to give the title compound as an off-white solid m.p. 181°–185°.

(c) 4-Acetylamino N-[2-(4-Hydrazinophenyl)ethyl]-benzeneacetamide hydrochloride The compound of Section (b) (6.25 g) was suspended in a mixture of water (17 ml) and concentrated hydrochloric acid (8.5 ml). The mixture was cooled in an ice bath and a solution of sodium nitrite (1.39 g) in water (8.5 ml) was added dropwise. The reaction mixture was stirred in the ice bath for 10 min to give a yellow solution with a fine suspension. The suspension was removed by filtration and the filtrate was collected in a cool receiver. The fltrate was poured into a solution of tin (II) chloride (20.6 g) in concentrated hydrochloric acid (8.5 ml) to give a yellow gum, which was removed and dissolved in ethanol (100 ml). The ethanol solution was evaporated in vacuo and re-evaporation with toluene gave a yellow gum. This gum was triturated with ER (250 ml) to give the title compound (9.36 g) as a pale yellow solid.

(d) The compound of Section (c) (252 mg) was dissolved in aqueous 25% acetic acid (4 ml) Dimethylaminobutanal diethylacetal (131 mg) was added and the mixture was heated at 80° for 2.5 h. The cooled reaction mixture was poured into EA (10 ml) and 2N NaOH solution (10 ml). The aqueous layer was saturated with K$_2$CO$_3$ and the layers were separated. The organic layer was discarded and the aqueous layer was extracted with ethanol (15 ml). The ethanolic extract was evaporated in vacuo to give an orange gum, which was suspended in (C) and flash chromatographed (C) to give the title product (40 mg) as a pale orange gum. T.l.c. (C), Rf 0.13.

EXAMPLE 30

(a) 4-(Acetylamino)-N-[2-[3-(cyanomethyl)-1H-indol-5-yl]ethyl]benzeneacetamide The compound of Example 29 Section (c) (1.5 g) was suspended in aqueous 25% acetic acid (10 ml) and 3-cyanopropanal diethyl acetal (0.237 g) was added. The mixture was heated at 80° for 2.5 h. The cooled reaction mixture was poured into NaOH solution (2N, 15 ml) and EA (15 ml) cooled in an ice-bath. K$_2$CO$_3$ (2 g) was added portionwise and the layers were separated. The aqueous layer was washed with EA (25 ml) and the combined organic extracts were dried (MgSO$_4$) and evaporated in vacuo to give a yellow oil. The oil was dissolved in CH$_2$Cl$_2$/ethanol/aqueous NH$_3$ (200:8:1) and flash chromatographed using the same solvent system to give the title compound (33 mg) as a white solid, m.p. 187.5°–189°.

(b) The compound of Section (a) (23 mg) was dissolved in dimethylamine in ethanol solution (33% w/w, 10 ml), and the resulting solution was added to the pre-reduced suspension of 10% PdO/C (50% aqueous paste, 40 mg) in ethanol (10 ml). The mixture was hydrogenated at 1 atmosphere hydrogen for 18 h. The catalyst was removed by filtration and the filtrate was evaporated in vacuo to give the title product (25 mg) as a clear gum. T.l.c. (C), Rf 0.15.

EXAMPLE 31

N-[2-[3-[2-(dimethylamino)ethyl]-1H-indol-5-yl]ethyl]-4-methoxybenzene acetamide

(a) N-[2-[3-(2-Hydroxyethyl)-1H-indol-5-yl]ethyl]-4-methoxybenzeneacetamide Intermediate 17 (366 mg) was stirred at room temperature under nitrogen with 2,3-dihydrofuran (0.09 ml) in ethanol:water (5:1) (12 ml) for 2 h. Hydrochloroic acid (2N; 10 drops) was added and the solution was heated at reflux for 22 h. The solution was basified to pH 8 using NaHCO$_3$ (8% solution; 3 ml) and the ethanol was removed under reducd pressure. The resultant aqueous suspension was extracted with EA (2×20 ml) then the combined extracts were washed with saturated NaCl solution (20 ml), and evaporated in vacuo to give a foam. Purification by 'flash' column chromatography, eluent ethyl acetate, gave the title compound as a foam (170 mg). T.l.c. (EA), Rf 0.25.

(b) N-[2-[3-(2-Bromoethyl)-1H-indol-5-yl]ethyl]-4-methoxybenzeneacetamide

Triphenylphosphine (149 mg) in dry CH$_2$Cl$_2$ (0.5 ml) was added dropwise at −10° to −5° under nitrogen to a stirred solution of the compound of section (a) (155 mg) and CBr$_4$ (139 mg) in dry CH$_2$Cl$_2$ (10 ml). After stirring at room temperature for 20 h (overnight) the solution was evaporated in the presence of silica gel and the resultant fine powder was chromatographed [elution with EA:hexane (1:1)] to give the title compound as a pale yellow viscous oil (117 mg). T.l.c. EA, Rf 0.51 (major).

(c) A solution of the product of Section (b) (117 mg) in ethanolic dimethylamine (33% w/w; 10 ml) was stirred at room temperature for 19 h. The solvent was removed in vacuo and the residue purified by 'flash' chromatography (C) to give the title compound of the invention as a colourless oil (96 mg). T.l.c. (C), Rf 0.27.

EXAMPLE 32

N-[2-[3-[2-(Dimethylamino)ethyl]-1H-indol-5-yl]ethyl]-4-methoxybenzeneacetamide

To a stirred solution of the compound of Example 20 (37 mg) in methanol (2 ml) solutions of $NaBH_4$(19 mg) in water (0.5 ml) and HCHO (0.07 ml of a 37–40% aqueous solution) in methanol (0.5 ml) were added dropwise simultaneously maintaining the temperature at 9°–10°. After stirring for 1.5 h solid $K_2CO_3$ was added to the solution until 2 layers were observed. The methanolic layer was separated and concentrated (to about 1 ml) in vacuo, then chromatography (H) grading to (C) gave the title compound as a colourless oil (25 mg). T.l.c. (C) (50:8:1), Rf 0.27.

EXAMPLE 33

N-[2-[3-[2-(Dimethylamino)ethyl]-1H-indol-5-yl]ethyl]-4-methoxybenzeneacetamide

A solution of Intermediate 19 (37 mg) in ethanolic dimethylamine (10 ml, 33% w/w) was hydrogenated over pre-reduced dry 10% PdO/C (40 mg) in absolute ethanol (7 ml) at room temperature and atmospheric pressure for 120 h. The catalyst was removed by filtration and the filtrate was evaporated in vacuo. The residue was purified by chromatography (C) to give the title compound (14 mg) as a colourless oil. T.l.c. (C), Rf 0.29.

TABLE

The following N.M.R. data was obtained for the compounds shown: Spectra were run in deuterated dimethylsulphoxide

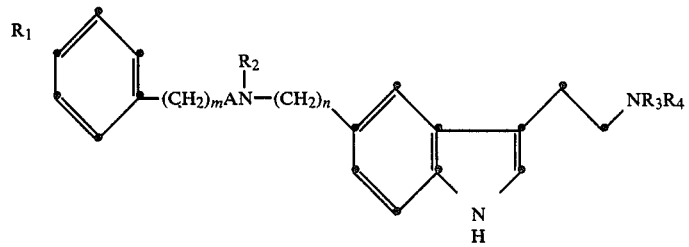

| Compound of Example No. | $R_1$ | $(CH_2)_m$ | $R_2$ δ(ppm) includes | $(CH_2)_n$ | $R_3R_4$ |
|---|---|---|---|---|---|
| 5 | 7.33, 7.98; 8.0, brs, 1H | 3.5, s, 2H | 8.22, brt, 1H | 2.8, m | 2.26, S, 6H, 2.82, d |
| 6 | 3.03, s | 4.1, s, 2H | — | 3–3.3 | 2.72, s, 6H |
| 7 | 2.98, s, 3H | 3.38, s | 8.16, t, 1H | 3.3–3.4, m; 2.75–2.85, m | 2.8, s |
| 11 | 2.88, s, 3H; 4.13, d, 2H; 7.57, t, 1H | 3.4, s, 2H | 8.18, t, 1H | 2.8, m; 3.3, m | 2.82, s |
| 12 | 7.53 + 8.12(2 × brs, 2 × 1H) | — | 8.77, t, 1H | 1.91, m, 2H; 2.73, t; 3.34, m | 2.81, s |
| 13 | — | 3.51, s, 2H | 8.31, brt, 1H | 2.80, m; 3.34, m | 2.85, s |
| 14 | 1.88, s, 3H; 4.21, d, 2H; | 3.38, s | 8.13, t, 1H | 3.30, m, 2H; 2.70, t, 2H | 2.68, s, 6H |
| 16a | 3.72, s, 3H | 2.36, t, 2H; 2.76, m | 7.96, t, 1H | 3.3, m; 2.76, m | 2.82, s |
| 16b | 2.96, s, 3H; 9.63; brs, 1H | 2.37, t, 2H; 2.77, m | 7.98, t, 1H | 2.77, m; 3.3, m | 2.83, s |
| 16c | 2.03, s, 3H; 9.91, s, 1H | 2.37, t, 2H; 2.77, m | 7.79, t, 1H | 3.3, m; 2.76, m | 2.85, s, 6H |
| 16d | 2.97, s | 2.08, t, 2H; 2.50, t; 1.75, m, 2H | 7.92, t, 1H | 2.79, t, 2H; 3.31, m | 2.70, s, 6H |
| 17 | 2.79, d; 3.38, s, 2H; 7.98, brq, 1H | 3.37, s | 8.15, brt, 1H | 2.85, m; 3.3, m | 2.72, s |
| 18 | 2.05, s; 9.85, s, 1H | 2.07, m; 2.48, m; 1.76, m, 2H | 7.91, brt, 1H | 2.8, t; 3.31, m, 2H | 2.45, s |
| 19 | 2.0–2.1, 2 × s, 3H(rotamers) | 3.22, s | 2.97 + 2.91, 2 × s | 3.55, m; 2.82, m | 2.77 + 2.79, 2 × s, 6H |
| 20 | 3.73, s, 3H | 3.32, s | 8.09, brt, 1H | 2.79, t; 3.3, m, 2H | — |
| 21a | 3.72, s, 3H | 3.32, s | 8.11, brt, 1H | 3.32, m; 2.78, t, 2H | $R_4$ 2.59, s, 3H |
| 21b | 3.72, s, 3H | 3.33, s | 8.11, brt, 1H | 3.32, m; 2.78, t, 2H | $R_4$ 2.96, 9, 1.19, t, 3H |
| 22 | 2.11, s, 3H | 3.4, s | — | 3.46, t; 2.83, t | — |

The analytical data below was obtained for the compounds prepared according to the Examples shown:

| Example No. | Analysis Found C | H | N | % |  | requires | C | H | N | % |
|---|---|---|---|---|---|---|---|---|---|---|
| 1 | 64.1 | 6.7 | 8.7 | | $C_{23}H_{29}N_3O_2.C_2H_2O_4$ | requires | 63.95 | 6.65 | 8.95 | |
| 2 | 62.2 | 6.8 | 11.1 | | $C_{24}H_{30}N_4O_2.C_2H_2O_4$ | requires | 61.6 | 6.7 | 10.8 | |
| 3 | 58.3 | 6.5 | 9.4 | | $C_{24}H_{30}N_4O_2.C_4H_6O_6.0.9H_2O$ | requires | 58.6 | 6.8 | 9.6 | |
| 4 | 61.5 | 6.4 | 9.8 | | $C_{22}H_{26}N_3O.HCl.0.5H_2O$ | requires | 61.5 | 6.5 | 9.8 | |
| 5 | 59.0 | 6.6 | 11.8 | | $C_{23}H_{28}N_4O_2.1.25HCl.1.5H_2O.0.2C_2H_5OH$ | requires | 59.2 | 6.9 | 11.8 | |
| 6 | 51.3 | 6.5 | 10.6 | | $C_{22}H_{30}N_4O_4S_2.HCl.0.2C_2H_5OH$ | requires | 51.3 | 6.2 | 10.7 | |
| 7 | 55.8 | 5.8 | 10.2 | | $C_{23}H_{30}N_4O_3S.C_2H_2O_4.0.38H_2O$ | requires | 55.7 | 6.1 | 10.4 | |
| 8 | 58.9 | 6.4 | 12.5 | | $C_{24}H_{30}N_4O_2.C_2H_2O_4$ | requires | 62.9 | 6.5 | 11.3 | |
| 9 | 61.8 | 6.4 | 10.9 | | $C_{24}H_{30}N_4O_2.C_2H_2O_4.0.17C_2H_5OH.0.1H_2O$ | requires | 62.5 | 6.6 | 11.1 | |
| 10 | 61.9 | 6.5 | 10.8 | | $C_{24}H_{30}N_4O_2.C_2H_2O_4.0.17C_2H_5OH.0.1H_2O$ | requires | 62.5 | 6.6 | 11.1 | |
| 11 | 56.2 | 5.9 | 9.8 | | $C_{24}H_{32}N_4O_3S.1.1C_2H_2O_4.0.14H_2O$ | requires | 56.4 | 6.2 | 10.0 | |
| 12 | 61.0 | 6.4 | 11.3 | | $C_{23}H_{28}N_4O_2.C_2H_2O_4.0.7H_2O$ | requires | 60.7 | 6.4 | 11.3 | |
| 13 | 54.5 | 6.0 | 10.6 | | $C_{22}H_{28}N_4O_3S.C_2H_2O_4.0.41H_2O.0.17$ | | | | | |

TABLE-continued

| | | | | | | | | |
|---|---|---|---|---|---|---|---|---|
| | | | | ethyl acetate | requires | 54.8 | 6.0 | 10.4 |
| 14 | 57.3 | 6.6 | 8.9 | $C_{25}H_{32}N_4O_2 \cdot 1.35C_4H_6O_4 \cdot 0.52H_2O$ | requires | 57.7 | 6.6 | 8.9 |
| 15 | 60.3 | 6.9 | 9.3 | $C_{26}H_{39}N_4O_2 \cdot C_4H_6O_6 \cdot 0.57H_2O$ | requires | 60.6 | 7.0 | 9.4 |
| 16a | 64.7 | 6.9 | 8.6 | $C_{24}H_{31}N_3O_2 \cdot C_2H_2O_4$ | requires | 64.6 | 6.9 | 8.7 |
| 16b | 55.8 | 6.3 | 9.7 | $C_{24}H_{32}N_4O_3S \cdot C_2H_2O_4 \cdot 0.5H_2O$ | requires | 56.2 | 6.3 | 10.1 |
| 16c | 59.9 | 6.5 | 9.8 | $C_{25}H_{32}N_4O_2 \cdot 1.6C_2H_2O_4 \cdot 0.2H_2O$ | requires | 59.6 | 6.3 | 9.9 |
| 17 | 58.6 | 6.9 | 8.9 | $C_{25}H_{32}N_4O_2 \cdot 1.2C_4H_6O_6 \cdot 0.3$ ethyl acetate. $0.58H_2O$ | requires | 58.4 | 6.8 | 8.8 |
| 18 | 64.9 | 7.7 | 10.2 | $C_{26}H_{34}N_4O_2 \cdot C_4H_6O_4$ | requires | 65.2 | 7.3 | 10.1 |
| 19 | 63.1 | 7.0 | 10.5 | $C_{25}H_{32}N_4O_2 \cdot C_2H_2O_4 \cdot 0.6C_2H_6O$ | requires | 62.9 | 7.0 | 10.4 |
| 20 | 61.1 | 6.5 | 8.6 | $C_{21}H_{25}N_3O_2 \cdot 1.1C_2H_2O_4 \cdot 0.26H_2O \cdot 0.1C_4H_{10}O$ | requires | 61.3 | 6.3 | 9.0 |
| 21a | 63.1 | 6.5 | 9.1 | $C_{22}H_{27}N_3O_2 \cdot C_2H_2O_4$ | requires | 63.3 | 6.4 | 9.2 |
| 21b | 64.0 | 6.7 | 9.0 | $C_{23}H_{29}N_3O_2 \cdot C_2H_2O_4$ | requires | 64.0 | 6.7 | 9.0 |
| 22 | 65.5 | 6.7 | 12.7 | $C_{22}H_{26}N_4O_2 \cdot 0.5C_4H_6O_4 \cdot 0.15H_2O$ | requires | 65.5 | 6.7 | 12.7 |

The following examples illustrate pharmaceutical formulations according to the invention containing 4-(acetylamino)-N-[2-[3-[2-(dimethylamino)-ethyl]-1H-indol-5-yl]ethyl]benzeneacetamide oxalate as the active ingredient. Other compounds of the invention may be formulated in a very similar manner.

| TABLETS FOR ORAL ADMINISTRATION DIRECT COMPRESSION | mg/tablet |
|---|---|
| Active ingredient | 2.4 |
| Calcium hydrogen phosphate B.P.* | 95.10 |
| Croscarmellose sodium USP | 2.00 |
| Magnesium stearate, B.P. | 0.50 |
| Compression weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

| INJECTION FOR INTRAVENOUS ADMINISTRATION | |
|---|---|
| | mg/ml |
| Active ingredient | 0.6 mg |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim:

1. Compounds of the formula (I):

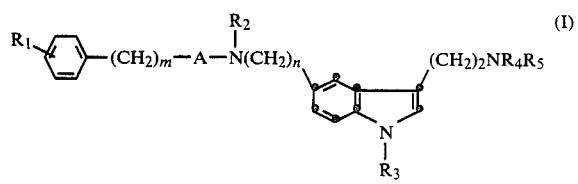

wherein
$R_1$ is a $H_2NCOCH_2-$, $CH_3NHCOCH_2-$, $(CH_3)_2NCOCH_2-$, $CH_3CONH-$, $CH_3CONHCH_2-$, $H_2NSO_2-$, $CH_3SO_2NH-$ or $CH_3SO_2NHCH_2$-group;
$R_2$ represents a hydrogen atom or a $C_{1-3}$alkyl group;
$R_3$ represents a hydrogen atom or a $C_{1-3}$alkyl group;
$R_4$ and $R_5$ which may be the same or different each represents a hydrogen atom, a $C_{1-3}$alkyl group or a 2-propenyl group;
A represents $-CO-$ or $SO_2-$;
n represents an integer from 2 to 5; and m represents zero or an integer from 1 to 4; and physiologically acceptable salts and solvates thereof.

2. A method of treating a patient susceptible to or suffering from migraine which comprises administering to the patient an effective amount of a compound of formula (I) as defined in claim 1 or a physiologically acceptable salt or solvate thereof.

3. A pharmaceutical composition which comprises at least one compound of formula (I) as defined in claim 1 or a physiologically acceptable salt or solvate thereof together with one or more physiologically acceptable carriers or excipients.

4. Compounds according to claim 1, wherein, in the formula (I), m represents the integer 1 and n represents the integer 2.

5. Compounds according to claim 1, wherein, in the formula (I), $R_2$ and $R_3$ each represents a hydrogen atom.

6. Compounds according to claim 1, wherein, in the formula (I), $R_4$ and $R_5$, which may be the same or different each represents a hydrogen atom or a methyl or ethyl group.

7. Compounds according to the formula (Ia):

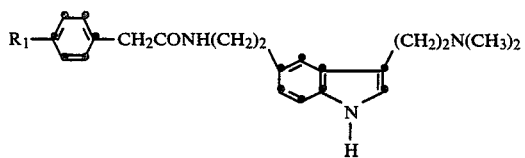

in which

R$_1$ is a H$_2$NCOCH$_2$—, CH$_3$NHCOCH$_2$—, (CH$_3$)$_2$NCOCH$_2$—, CH$_3$CONH—, CH$_3$CONHCH$_2$—, H$_2$NSO$_2$—, CH$_3$SO$_2$NH— or CH$_3$SO$_2$NHCH$_2$— group;

and physiologically acceptable salts and solvates thereof.

8. Compounds according to claim 7, wherein, in the formula (Ia), R$_1$ is a H$_2$NCOCH$_2$—, CH$_3$NHCOCH$_2$—, CH$_3$SO$_2$NHCH$_2$—, or H$_2$NSO$_2$— group.

9. 4-(Acetylamino)-N-[2-[3-[2-(dimethylamino)ethyl-1H-indol-5-yl]ethyl]benzeneacetamide and its physiologically acceptable salts and solvates.

10. A method of treating a patient susceptible to or suffering from migraine which comprises administering to the patient a pharmaceutical composition as claimed in claim 3.

* * * * *